United States Patent [19]
Kirkpatrick et al.

[11] Patent Number: 5,840,700
[45] Date of Patent: Nov. 24, 1998

[54] METHODS OF PRODUCING TRANSFER FACTOR

[75] Inventors: Charles H. Kirkpatrick, Denver; Stephen J. Rozzo, Aurora, both of Colo.

[73] Assignee: National Jewish Center for Immunology and Respiratory Medicine, Denver, Colo.

[21] Appl. No.: 441,973

[22] Filed: May 16, 1995

Related U.S. Application Data

[62] Division of Ser. No. 279,278, Jul. 22, 1994, Pat. No. 5,470,835, which is a continuation of Ser. No. 20,244, Feb. 19, 1993, abandoned, which is a continuation of Ser. No. 718,571, Jun. 26, 1991, abandoned, which is a continuation-in-part of Ser. No. 547,500, Jul. 2, 1990, abandoned.

[51] Int. Cl.$^6$ .................................................. C07K 17/00
[52] U.S. Cl. ........................ 514/21; 530/344; 530/351; 530/413; 530/417
[58] Field of Search ................................... 530/344, 351, 530/300, 413, 417; 514/21

[56] References Cited

PUBLICATIONS

Pandey, "Purification of nucleotide linked peptide" Caplus AB# 1988:469727 1988.

Freifelder, "Physical Biochemistry, 2nd Edition" pp. 216–225, 225–265 +494–524. 1982.

Kirkpatrick "Murine Transfer Factors III." J. Immunol. 135 (6) pp. 4027–4033 1985.

Qi, H. Y. et al. "Chemical Characterization of the Purified Component of Specific Transfer Factor in the Leukocyte Dialysates from HSV–1 Immunized Goats" *Acta viro.*, vol. 36, pp. 239–244 (1992).

Biemann, K. "Methods for Protein Sequencing", *Analytical Chemistry*, vol. 58, No. 13, pp. 1289A–1300A (1986).

*Primary Examiner*—Cecilia J. Tsang
*Assistant Examiner*—Patrick R. Delaney
*Attorney, Agent, or Firm*—Jones & Askew

[57] ABSTRACT

The invention relates to substantially pure transfer factor with a specific activity of at least 5000 units per absorbance unit at 214 nm. The present invention also relates to a process for preparing the transfer factor from cell lysates. The present invention includes the use of substantially pure transfer factor with a specific activity of at least 5000 units per absorbance unit at 214 nm to treat infectious diseases.

24 Claims, 17 Drawing Sheets

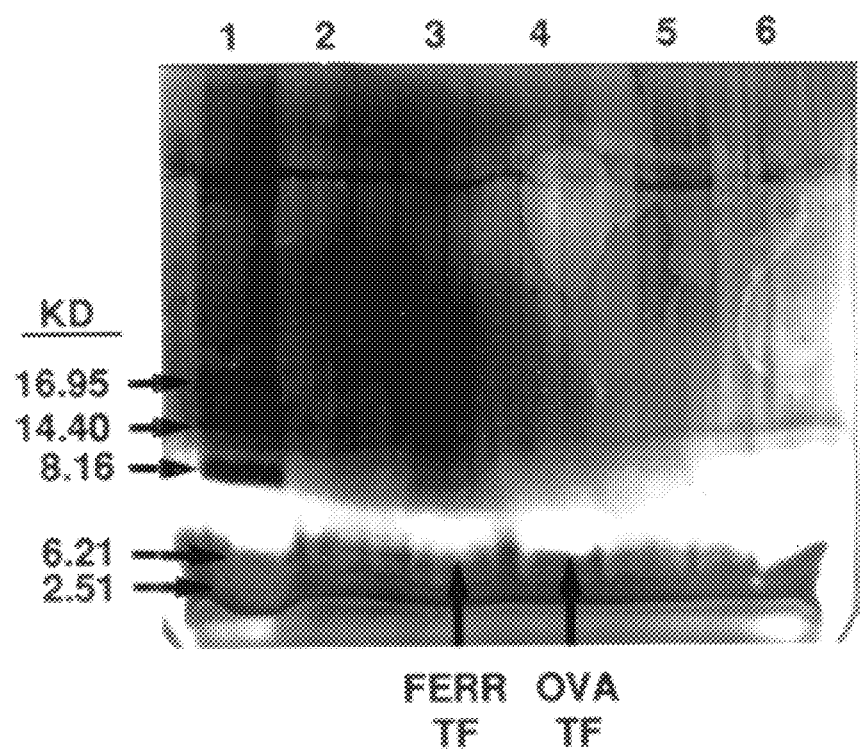
Fig_17

1

METHODS OF PRODUCING TRANSFER FACTOR

CROSS-REFERENCE TO RELATED APPLICATIONS

This application is a divisional of U.S. application Ser. No. 08/279,278 filed Jul. 22, 1994, now issued as U.S. Pat. No. 5,470,835, which is a continuation of U.S. application Ser. No. 08/020,244 filed Feb. 19, 1993, now abandoned, which is a continuation of U.S. application Ser. No. 07/718, 571 filed Jun. 26, 1991, now abandoned, which is a continuation-in-part of U.S. application Ser. No. 07/547,500 filed Jul. 2, 1990, now abandoned.

FIELD OF INVENTION

This invention relates to the transfer of cell-mediated immunity by administering substantially pure transfer factors to a human or animal. More particularly, it relates to processes for obtaining the substantially pure transfer factors, the substantially pure transfer factors themselves, and methods of using the substantially pure transfer factors to treat diseases.

BACKGROUND OF THE INVENTION

The terms "antigenic determinant" and "epitope" are defined as the parts of a molecule that can interact specifically with either the cellular or the humoral products associated with the immune response. The term "antigen" is defined as anything that can serve as a target for an immune response. The immune response can be either cellular or humoral. The term "cell mediated immunity" is defined as an immune response mediated by cells rather than by antibody. The term "delayed type hypersensitivity" is defined as a T-lymphocyte-mediated inflammatory response that occurs in close proximity to the site of injection or application of the inciting antigen. It includes, but is not limited to, delayed type hypersensitivity and cytotoxic T cells. A "hapten" is defined herein as a substance that reacts selectively with appropriate antibodies or T cells but the hapten itself is usually not immunogenic. Most haptens are small molecules or small parts of large molecules, but some macromolecules can also function as haptens. The term "antibody" means molecules that also bind antigens, however, they are distinguished from transfer factor in that the molecular weight of antibodies is between approxiamtely 160,000 Daltons and 1,000,000 Daltons.

Transfer factors have been defined as a dialyzable material or family of materials that can be extracted from lymphoid cells of humans and certain other animals and have the capacity to transfer immune responses from one individual to another, even across species. The material is a substance obtained from leukocytes, usually lysed, from humans and other vertebrates that have been sensitized so as to express delayed type hypersensitivity or other cell mediated responses to a sensitizing antigen. Transfer factor binds homologous antigen and has the capacity to mediate transfer of delayed type hypersensitivity and other cell mediated immune responses from one individual to another. In such a situation the individual from whom the transfer factor is obtained has been sensitized to the antigen of interest.

Notwithstanding the above properties, the transfer factors are smaller than antibodies, and do not transfer antibody mediated responses, nor do they induce antibody production.[1,2,3] These properties of transfer factor are also described by Spitler et al. which discusses a "transfer factor" secured from the leukocytes of healthy donors.[4] The material suppresses disease symptoms. Spitler et al. describe the material as being heat stable, and having a molecular weight of less than 20,000 Daltons. It is secured by lysing leukocytes, and then incubating the lysate with $Mg^{+2}$ and DNase, followed by filtration through a millipore filter.

1 Kirkpatrick et al., *J. Immunol.* 134: 1723–1727 11985)
2 Peterson et al., *J. Immunol.* 126: 2480–2484 (1981)
3 Burger et al., *Cell Immunol.* 29: 410–413 (1977)
4 U.S. Pat. No. 3,991,182 to Spitler, et al.

There have been numerous additional attempts to characterize the substance referred to as transfer factor, these being reported in both the scientific and patent literature. In all of these reports, the transfer factor material was a crude fraction of cell lysate. To the inventors knowledge, no one has produced a substantially pure transfer factor. Baram et al. fractionated human leukocyte extracts through ion exchange chromatography, using diethylaminoethyl cellulose (DEAE).[5] This work was continued and, as reported by Baram et al., gel filtration and paper chromatography were used to further fractionate human leukocyte extracts.[6] Among the conclusions presented by this work was that transfer factor contained nucleosides. Work by Lawrence et al. using gel filtration chromatography on leukocyte extracts of sensitized humans, led to a proposal that transfer factor is (i) water soluble, (ii) dialyzable, (iii) has a molecular weight of less than 10,000 Daltons, (iv) was resistant to deoxyribonuclease, ribonuclease and trypsin digestion, and (v) possessed a chromatoaraphic peak showing greater absorbance at 260 nm than at 280 nm.[7,8,9] This combination of factors led to a proposal that transfer factor was a small, ribonuclease resistant polyribonucleotide.

5 Baram et al., *J. Allergy* 33: 498–506 (1962)
6 Baram et al. *J. Immunol.* 97: 407–420 (1966)
7 Lawrence et al., *J. Clin. Invest.* 34: 219–232 (1955);
8 Lawrence et al., *J. Exp. Med.* 104: 321323 (1956)
9 Lawrence et al., *Trans. Assoc. Amer. Physicians* 76: 84–89 (1963)

Progress toward the molecular characterization of transfer factors has been slow, limited largely by the lack of an adequate purification methodology and the need for quantitative assay methods. It has been shown that molecules having transfer factor activity are relatively small, i.e. less than 6000 Daltons, hydrophilic, and polar in native form. Furthermore, transfer factor activity survives heating at 56° C., but not at 75° C., for 30 minutes, and at least brief exposure to 95% ethanol. Results from enzyme sensitivity and activity depletion studies have produced results compatible with a nucleopeptide or nucleoprotein model for the structure of transfer factors. Caution must be used in interpreting prior art results, however, because impure preparations were studied and quantitative determinations were not performed. Thus, the molecular nature of transfer factors is, as yet, not well understood.

The inclination toward the assumption that a nucleotide or nucleoside was a part of the transfer factor molecule was continued by Gottlieb et al.[10,11,12] Gottlieb differentiated transfer factors from immune modulators (the '379 patent), and amplifiers (the '079 patent). In the *Lancet* publication, Gottlieb postulated that transfer factor consisted of 12 amino acids and an oligonucleotide. As a result, research focused on the study of eluates at wavelengths of 254 nm or greater. Many reports noted high 254/260 nm to 280 nm absorbance ratios, again suggesting oligonucleotides as part of the transfer factor fraction.[13,14,15,16,17,18,19,20,21] Similarly, Warren hypothesizes a molecule of a molecular weight of from 5000 to 10,000 Daltons containing protein and RNA.[22] Goust et al. describes dialyzable transfer factor as a mixture of molecules of molecular weight generally from 4000 to 7000 Daltons and containing a ribonucleotide.[23] Again, Wilson et al.[24] describes three forms of transfer factor, all of which contain a nucleotide moiety and a peptide moiety. (Note column 11 of this reference.)

10 Gottlieb et al., *Lancet* 2: 822–823 (1973)
11 U.S. Pat. No. 4,468,379 to Gottlieb, et al.
12 U.S. Pat. No. 4,616,079 to Gottlieb, et al.
13 Arala-Chaves et al., *Int. Arch. Allergy* 31: 353–365 (1967)
14 Neidhart et al., *Cell Immunol.* 9: 319–323 (1973)
15 Reymond et al., *Vox sang.* 29: 338–351 (1975)
16 Dunnick et al., *Proc. Natl. Acad. Sci.* USA 72: 4573–4576 (1975)
17 Vandenbark et al., *J. Immunol.* 118: 636–641 (1977)
18 Dunnick et al., *J. Immunol.* 118: 1944–1950 (1977)
19 Burger et al., *J. Immunol.* 122: 1091–1098 (1979)
20 Wilson, *Trans. Assoc. Amer. Physicians* 92: 239–256 (1979)
21 Borvak etal., *Acta Virol.* 29: 119–128 (1985)
22 U.S. Pat. No. 4,435,384 to Warren
23 U.S. Pat. No. 4,001,080 to Goust, et al.
24 U.S. Pat. No. 4,816,563 to Wilson, et al.

The progress that has been made in characterizing the impure transfer factor material is summarized in a review by Kirkpatrick.[25] In that review, the dialyzable material that contains transfer factor activity is described as a polypeptide with a molecular weight of between 4000 and 6000 Daltons and is protease sensitive. The transfer factor material apparently binds specifically to antigen.[26] The review states that the presence of nucleic acids, ribose, and phosphodiester groups has not been ruled out.[27] Thus, the physical characteristics of the transfer factor material could not be definitively determined because substantially pure material had not been isolated.

25 Kirkpatrick, *J. Allergy Clin Immunol*, 81:803–813, 1988
26 Borkowsky,et al., *J. Immunol.* 126:486–489, 1981.
27 Kirkpatrick, "Transfer Factor" Supra. at page 808

It will be seen that the prior art in this field has suggested that transfer factor is a nucleotide/protein complex. However, because a substantially pure transfer factor has not been isolated, it is not possible to conclusively characterize the transfer factor material.

Interest in the molecule and its structure has, if anything, increased because of its therapeutic efficacy. Apart from therapeutic uses described by the references set forth above, reference may be made, e.g., to Viza et al.[28] suggesting transfer factor therapy for *Herpes simplex* virus. One also notes Warren[29], describing dermatological efficacy for blemishes, acne, condyloma and HSV. The transfer factor fraction has been shown to be efficacious against *C. albicans*, as shown in Kirkpatrick et al,[30] the disclosure of which is incorporated by reference. Additional showings of efficacy against *Herpes simplex* may be found.[31,32,33] *Varicella zoster* infection has been prevented with transfer factor.[34] Transfer factor has showed efficacy against cryptosporidiosis in AIDs patients.[35,36] All of these studies were performed with only partially purified transfer factor fractions. No clinical or biochemical studies have been performed to date with substantially pure transfer factor material because of the difficulty in isolating and characterizing pure transfer factor material.

28 European Patent Application 101,200 to Viza et al.
29 U.S. Pat. No. 4,435,384
30 Kirkpatrick et al., in Khan et al., ed., *Immune Regulators In Transfer Factor*, pg. 547–559 (Academic Press, 1979)
31 Khan et al., *Dermatologica* 163: 177–185 (1981)
32 Dwyer in Kirkpatrick et al., *Immunobiology of Transfer Factor*, pg. 233–243 (Academic Press, 1983)
33 Viza et al., *Lymphokine Res* 4: 27–30 (1985)
34 Steele et al., *New Eng. J. Med.* 303: 355–359 (1980)
35 Louie, et al., *Clin. Immunol. Immunopath* 44: 329–334 (1987)
36 McMeeking et al., *J. Infect. Dis* 161: 108–112 (1990)

As can be seen by the foregoing review of the literature on transfer factor, the isolation and characterization of a substantially pure transfer factor material has eluded the research community for over thirty years. Despite keen scientific and clinical interests, and after deducing several important physical parameters about the elusive transfer factor material, the actual physical isolation of substantially pure material has not been possible.

What is needed is substantially pure transfer factor material. With substantially pure material in hand, it would be possible to sequence the material and produce the material either chemically or by recombinant methods. These molecules could then be administered to humans or animals thereby transferring immunity to a specific antigen or epitope. Substantially pure transfer factor could be made to treat already infected humans or animals or could be used to prevent disease. Isolation and purification of substantially pure transfer factor would be of great benefit to the treatment of disease.

SUMMARY OF THE INVENTION

The present invention provides for purified transfer factor, a method of producing purified transfer factor, and methods of treating various diseases with the purified transfer factor. Because the purification methods disclosed in this application apply to the isolation of any transfer factor that is specific for any antigen, it is contemplated that the present invention includes any substantially pure transfer factor with a specific activity greater than 5,000 units per $AU_{214}$. It is estimated that the prior art transfer factor preparations known to the inventor have a specific activity of no more than approximately 1,000 units per absorbance unit at 214 nm.

The present invention includes substantially pure transfer factors that are isolated from natural sources or are produced synthetically. Substantially pure transfer factors from either source can be used according to the present invention to treat a wide variety of pathological conditions. For example, a transfer factor or factors that transfer cell mediated immunity against *Herpes simplex* virus can be used either to treat a *Herpes simplex* infection or to protect a human from *Herpes simplex* infection.

The advantages of using transfer factors to impart immunity are many. They include speed of transfer of immunity. Immunity to a specific antigen can be detected in as little as several hours after administration of the transfer factor. This is a vast improvement over conventional immunization which can take weeks or months to impart protection.

Because each unique transfer factor molecule is thought to transfer immunity to a specific antigen or epitope, several different transfer factor molecules specific for different antigens can be admixed to custom design a complex immune response.

The substantially pure transfer factor allows one to determine the amino acid sequence of a particular transfer factor and, given this information, one can synthesize the transfer factor either chemically or by recombinant methods. Thus, as a result of the present invention, large quantities of transfer factor can now be produced. This will allow transfer of a desired immune response to large numbers of humans or animals.

In addition, the storage of transfer factor is another advantage. Transfer factor molecules that are contemplated as part of the present invention are very stable. Thus, according to the present invention, the transfer factor molecules do not require extraordinary precaution to maintain or administer the material.

Accordingly, it is an object of the present invention to provide a substantially pure transfer factor.

It is another object of the present invention to provide a substantially pure transfer factor with a specific activity of at least 5000 units per $AU_{214}$.

It is yet another object of the present invention to provide a substantially pure transfer factor that can be administered to a human or animal to transfer a desired immune response.

It is another object of the present invention to provide a method of producing a substantially pure transfer factor from cell lysate.

It is another object of the present invention to provide a substantially pure transfer factor for treating infectious diseases.

It is another object of the present invention to provide a substantially pure transfer factor for protecting against infectious diseases.

It is yet another object of the present invention to provide for a substantially pure transfer factor specific for viruses such as *Herpes simplex*, *Herpes zoster*, cytomegalovirus measles, HIV, and other viruses that cause disease in humans and animals.

It is another object of the present invention to provide for a substantially pure transfer factor specific for fungi such as *Candida albicans*, *Histoplasma capsulatum*, *Coccidioidies immitis*, and *Pneumocystis carinii*.

It is yet another object of the present invention to provide for a substantially pure transfer factor specific for mycobacteria including *Mycobacterium leprae*, *Mycobacterium tuberculosis*, and *Mycobacterium avium* complex.

It is yet another object of the present invention to provide for a substantially pure transfer factor specific for parasites such as cryptosporidia, isospora, leishmania species, Cocidioides and other parasites that infect humans and animals.

It is yet another object of the present invention to provide for a substantially pure transfer factor specific for protozoa.

It is yet another object of the present invention to provide for a substantially pure transfer factor that can be isolated from one species and used to transfer immunity to another species.

It is yet another object of the present invention to provide for a substantially pure transfer factor that can be administered orally.

These and other objects, features and advantages of the present invention will become apparent after a review of the following detailed description of the disclosed embodiment and the appended claims.

BRIEF DESCRIPTION OF THE FIGURES

FIG. 17 shows an SDS-polyacrylamide gel electrophoresis profile of transfer factor under non-reducing conditions.

DETAILED DESCRIPTION

Figure 1:
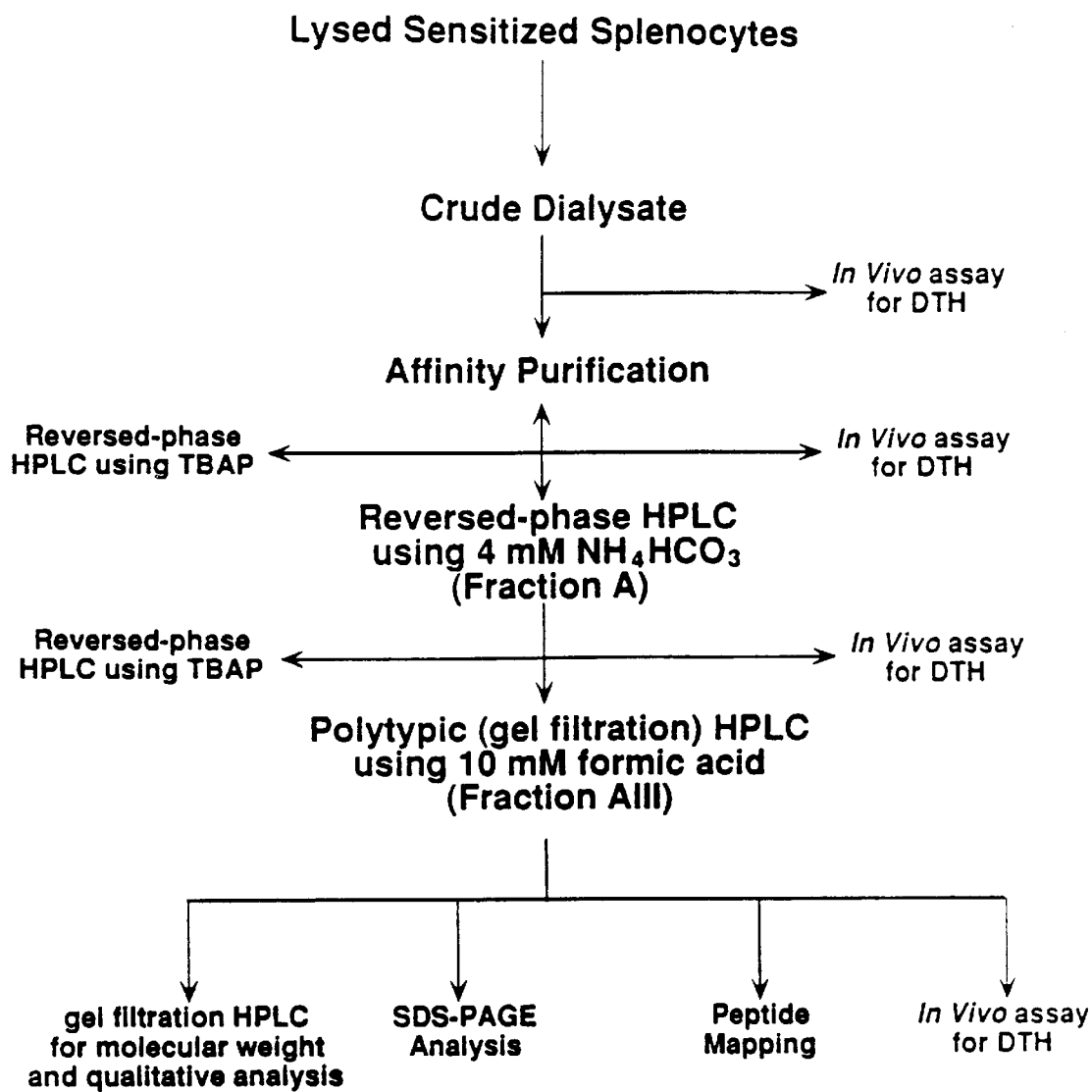
FIG. 1 is a schematic of the strategy used to purify transfer factor.

The present invention comprises a substantially pure transfer factor and a method for preparing substantially pure transfer factor from natural sources. The present invention also comprises methods of treating various diseases with the substantially pure transfer factor.

Specifically the present invention comprises a substantially pure transfer factor with a specific activity of at least 5000 units per $AU_{214}$. The preferred specific activity is at least 10,000 units per $AU_{214}$ with the most preferred specific activity of at least 20,000 units per $AU_{214}$ to 60,000 units per $AU_{214}$. The substantially pure transfer factor is a polypeptide with a molecular weight of approximately 4900 to 5500 Daltons. The substantially pure transfer factor can transfer delayed type cell mediated immunity to a non-immune human or animal.

The substantially pure transfer factor is effective in transfering cell mediated immunity in humans or animals for a wide variety of antigens or epitopes. The substantially pure transfer factor can be administered either by injection or can be administered orally. Injection can be intravenously, intramuscularly or subcutaneously or a combination of routes.

When injected, the dose of transfer factor required to impart immunity to a human is between approximately 1 ng and 500 ng with a preferred dose range of between 25 ng and 250 ng with a most preferred dose of approximately 50 ng. The optimal dose for any particular transfer factor will vary within the stated range.

There is strong evidence that immunity against certain viruses, especially the human Herpes viruses, is dependent upon the cell-mediated immune system. Activation of cell-mediated immunity with a specific transfer factor would be expected to improve the normal mechanisms that act to clear active viral infections. A similar activation of specific immunity by a transfer factor can provide protective immunity against the virus even before it is encountered. The latter proposal is supported by the report of Steele et al., in which children with acute leukemia were protected against chicken pox infections by administration of a *Varicella zoster* (chicken pox)-specific transfer factor fraction.[37] It is important to consider the rapidity of action of transfer factors. The recipients acquire specific immunity in 24 to 48 hours. This is much more rapid than the 2 to 6 weeks required for induction of immunity by conventional vaccines.

[37]Steele, et al. Supra

Tuberculosis, leprosy and infections caused by "atypical" mycobacteria (i.e., *Mycobacterium avium* complex) may produce immunodeficiency in the patients or may occur because the patient had an immune deficiency that allowed the organism to establish an infection. Similar evidence exists for certain fungal infections. There is evidence that many patients with these diseases have impaired cell mediated immunity and that these immune deficiencies may be corrected with a specific transfer factor.

Mechanisms of immunity to intestinal parasites are variable. However, AIDS, a disease in which cell-mediated immunity is severely impaired has provided evidence that certain parasitic diseases of man are related to cell-mediated immune responses. These include cryptosporidiosis and isosporosis. A placebo controlled, clinical trial of specific transfer factor in patients with intestinal cryptosporidiosis showed significant beneficial responses in the transfer factor recipients.[38]

[38]McMeeking et al., Supra

The observation of Steele, et al.[39] that chicken pox infections could be prevented by pretreatment of children with the appropriate transfer factor indicates an important role for transfer factors as agents to prevent certain infectious diseases. Because transfer factors activate the cell mediated immune system and act very rapidly, they provide an important novel approach to prophylactic immunity that is not provided by currently used vaccines (that are used because they stimulate antibody production). Specific examples include, but are not limited to:

a. prevention of varicella;

b. prevention of parasitic infections, i.e., cutaneous leishmaniasis, in travelers to endemic areas;

c. prevention of cytomegalovirus infections in recipients of organ transplants;

d. prevention of *Pneumocystis carinii* pneumonia in patients with cellular immunodeficiency because of viral infections (i.e., HIV) or immunosuppressive treatments;

e. prophylaxis against certain infectious diseases (i.e., leishmaniasis) that are endemic in certain geographic areas.

[39]Steele, et al., Supra

The substantially pure transfer factor of the present invention is useful in treating a wide variety of pathological conditions in both humans and animals. For example, the substantially pure transfer factor of the present invention can be used to treat or prevent viral infections, including, but not limited to, *Herpes simplex*, types I and II, Epstein-Barr virus, cytomegalovirus measles, human immunodeficiency virus (HIV), and other viruses that cause disease in humans and animals. The substantially pure transfer factor of the present invention can be used to treat or prevent fungal infections, including, but not limited to, *Candida albicans, Histoplasma capsulatum, coccidioidies immitis*, and *Pneumocystis carinii*. The substantially pure transfer factor of the present invention can be used to treat or prevent mycobacterium infections, including, but not limited to, *Mycobacterium leprae, Mycobacterium tuberculosis*, and *Mycobacterium avium* complex. The substantially pure transfer factor of the present invention can be used to treat or prevent parasitic infections including, but not limited to, cryptosporidia, isospora, leishmania species, coccidia, and other parasites that infect humans and animals.

Certain immunodeficiency syndromes are characterized by selective defects in cell-mediated immunity. Patients with these disorders are susceptible to infections with common ubiquitous microorganisms such as *Candida albicans*, herpes viruses, *Pneumocystis carinii* and certain intestinal parasites.

The immunologic deficiencies in certain diseases such as the Wiskott-Aldrich syndrome and chronic mucocutaneous candidiasis are genetically determined and usually are diagnosed within the first few years of life. Others are acquired through immunosuppressive treatments, immunosuppressive diseases or through unknown mechanisms.

Kirkpatrick, et al., have shown that specific transfer factor therapy corrects the immune deficiency in patients with chronic mucocutaneous candidiasis and these patients resist relapses after their infections are cleared with antifungal agents. Specific examples of immune deficiency diseases that can be treated with the substantially pure transfer factor of the present invention include, but are not limited to, a. chronic mucocutaneous candidiasis;

b. hyper IgE syndrome;

c. Wiskott-Aldrich syndrome;

Although not wanting to be bound by the following hypothesis, it is believed that transfer factors are specific for a particular antigen or epitope. Thus, each transfer factor molecule can transfer immunity to a specific epitope. It is believed from the data obtained from the substantially pure transfer factor made according to the present invention that each transfer factor molecule has a region with a constant amino acid sequence. In another region, the amino acid sequence is variable. It is the variable region that provides the specificity for a particular antigen.

By isolating a substantially pure transfer factor that is specific for a particular epitope, one can then sequence the transfer factor and, using the sequence data, produce the transfer factor in large quantities by either chemical synthesis or by recombinant technology.

In addition, it is contemplated as part of the present invention to produce large amounts of a substantially pure transfer factor from an immunized animal by the process described herein. This substantially pure transfer factor can then be used to transfer immunity to another, non-immune animal or human.

It is important to note that the substantially pure transfer factor according to the present invention can be produced from one species, for example, bovine, and the substantially pure transfer factor from the bovine source can successfully be used to transfer specific immunity to another species, for example, a human.

Although not wanting to be bound by the following hypothesis, results suggest transfer factors are produced by CD4+ (L3T4+) peripheral T cells. These experiments were performed by isolating macrophages, B cells, CD4+ T cells, and CD8+ T cells from actively-sensitized mice, preparing dialysates from these cells, and performing dose-response studies for transfer factor activity using these preparations in naive recipient mice. Comparison of the titration curves for each dialyzate preparation with data on the purity of each cell preparation (from cytofluorography) suggests that all transfer factor activity was contributed by CD4+ T cells. The major histocompatibility complex restricted production of transfer factors is compatible with the notion they are produced by T cells. It is believed that transfer factors are encoded by a set of germ-line genes in CD4+ cells which are rearranged through processes similar to those known to effect rearrangement of other antigen-specific molecules. The similar physicochemical properties of transfer factors of differing antigen specificities might suggest genes encoding constant and variable regions for transfer factors. It is further suggested that transfer factors are produced in a clonal manner, and that the transfer factor produced by a given T cell will have specificity for an epitope of the same antigen as the T cell receptor (TCR) on that T cell. Clonality for transfer factor production is compatible with the antigen-specific activity of transfer factors. In this regard, it is suggested that different amino acid residues on the same epitope-containing peptide are recognized by a transfer factor and its corresponding TCR.

Perhaps the most provocative issue raised by these proposals is the mechanism by which the random rearrangement of T cell receptor genes might be coordinated with the rearrangement of transfer factor genes. Implicit from this model is a specific signalling mechanism between TCR and transfer factor genes. There are no data for the coordination of a system as complex as this in the literature. In this regard, one can conceive of a unique set of trans-acting factors which regulate transfer factor gene rearrangement. Alternatively, one might envision antigen, recycled TCR, or fragments of one of these serving this purpose. Whatever the mechanism, this is one of the most enigmatic features for this model. As opposed to models of random transfer factor gene rearrangement, this model provides for the elimination of cells which might otherwise produce transfer factors with specificity for autologous antigens. That is, the clonal deletion of autoreactive T cells based on their TCR reactivity would also eliminate transfer factors having corresponding specificity. In this regard, Burnet[40] proposed a germ-line model for transfer factor genes, also proposing clonal production of transfer factors, as part of what is often called the "minireceptor hypothesis". Other than the issue of coordinated regulation of gene rearrangement, the present model closely resembles what is known for immunoglobulin and TCR gene organization and rearrangement.

40 Bunet, *J. Allergy and Clin. Immuno.* 54:1–13 (1974)

It is believed that transfer factors are not constitutively produced, and are not necessary for the induction of primary immune responses. Transfer factor activity in experimental in vivo systems is only evident for preparations from sensitized donors. At minimum, a 10,000-fold enhancement of transfer factor activity for such preparations is suggested. Also, the rapid (24 hour) induction of DTH responsiveness in transfer factor recipients is not consistent with a natural role for transfer factors in induction of primary immune responses.

It is believed that transfer factors can be obtained from memory T lymphocytes. The kinetics observed for transfer factor activity using in vivo experimental models (i.e., the induction of responsiveness within 24 h), are consistent with secondary immune response kinetics. The failure of transfer factors to induce in vitro T cell proliferation is compatible with the notion that memory T cells contain transfer factor activity. The diminution of memory T cell responses to antigen challenge in the absence of periodic antigen-driven T cell activation is compatible with a similar decline in the DTH responsiveness of transfer factor recipients with time under similar conditions. The rapid induction of DTH responsiveness subsequent to administration of highly purified transfer factors may suggest that these molecules play a pivotal role in secondary immune responses, which is also compatible with the notion transfer factors may be present in memory T cells.

In summary, it is believed that transfer factors are encoded by rearranged germ-line genes in CD4+ T cells. It is further believed that transfer factors are produced subsequent to primary, MHC-restricted sensitization and may be obtained from memory T cells.

It is believed that under natural conditions transfer factors are functional following MHC-restricted antigen presentation to appropriate transfer factor-containing T cells. Results from experimental in vivo models show transfer factors function in allogeneic, and even xenogeneic, recipients. In contrast, passive transfer of DTH using, cloned CD4+ T cells, which have been shown to mediate DTH, function in an MHC-restricted manner. These results may be reconciled by suggesting that administration of exogenous transfer factor in experimental in vivo models may circumvent an otherwise natural requirement for MHC-restricted antigen presentation before transfer factor functional activity is expressed.

It is further believed that following MHC-restricted antigen presentation to the TCR, transfer factors participate in reactions which lead to a secondary immune response phenotype for transfer factor-containing T cells. It is further believed that transfer factors may be released by transfer factor-containing T cells into the extracellular milieu, enter nearby naive T cells, and exert a similar effect on these cells as they do on transfer factor-producing cells. This would be compatible with results from experimental in vivo models showing, administration of exogenous transfer factor stimulates DTH responsiveness for naive recipient animals or humans, Entry into naive T cells might involve an as yet unidentified receptor on the surface of these cells which binds transfer factors. Burnet[41] proposed the existence of "minireceptors" which would be complementary in structure to transfer factors. Thus, for a transfer factor of a given antigen specificity there would exist a minireceptor which would bind that transfer factor specifically. For the model presented here, a non-polymorphic receptor is proposed. Although no evidence is available for such a transfer factor receptor, one might envision molecules, such as CD-45R, which are expressed in greater quantity on naive than memory T cells as candidates for the receptor.

41 Burnet, *Supra*

It is believed that transfer factors only function in T cells with specificity for antigen corresponding to that of the transfer factor. Thus, although any T cell in the vicinity of transfer factor-releasing T cells might have the ability to bind and take up any transfer factor, only those which have taken up the appropriate transfer factor and are subsequently presented with the appropriate antigen by syngeneic antigen presenting cells (APC) will respond to the transfer factor activity.

It is believed that transfer factors participate in T cell activation through specific binding of transfer factors to antigen. Results from study of the genetic regulation of transfer factor activity indicate transfer factors can confer a high responder phenotype to low responder mice in systems where tolerance is otherwise manifested through determinant selection mechanisms. In one experiment, DTH responsiveness was established for chicken ovalbumin or the ovalbumin immunodominant peptide in low responder CBA/J (H-$2^k$) mice using transfer factor preparations from high responder BALB/cBy (H-$2^d$) mice. It has been shown that the failure of H-$2^k$ mice to respond to this antigen is due to the inability of antigenic ovalbumin peptides to bind H-$2^k$ class II antigen. Additionally, the results indicate transfer factors bind intact protein antigens, including chicken ovalbumin, in a specific manner. Together, these results are compatible with a role for transfer factors in antigen presentation to T cells. This may occur through the formation of MHC product/transfer factor/antigen complexes on the surface of APC. Observations of transfer factor activity in allogeneic and xenogeneic systems might be compatible with the notion that transfer factors interact with conserved portions of MHC-encoded molecules distal to the antigen-binding cleft in a manner analogous to that proposed for superantigen binding to MHC products. Thus, an MHC-encoded molecule to which a transfer factor is bound distal to the antigen-binding cleft in an orientation which places transfer factor-bound antigen in the cleft might comprise the configuration of a functional MHC product/transfer factor/antigen complex.

Results from experimental in vivo models show that if transfer factors interact with intact, homologous antigen in solution prior to administration to recipients that transfer factor activity is abrogated. These results suggest that transfer factors must interact with immune system components prior to interaction with antigen. This would be compatible with results showing transfer factors must be administered prior to antigen challenge for DTH responses to be observed subsequently. Alternatively, this phenomenon may not be relevant under physiological conditions, and transfer factors may normally interact with antigen in vivo with full retention of transfer factor activity. The utility of a transfer factor antigen-binding function may be to reduce antigen competition for antigen presentation. That is, the binding of transfer factors to foreign antigens may facilitate the presentation of these antigens to T cells under conditions where an abundance of autologous antigens might otherwise compete effectively for binding with MHC molecules.

In summary, it is believed that transfer factor functional activity is enabled following MHC-restricted antigen presentation to transfer factor-containing T cells. This activity would be manifested in transfer factor-containing T cells through mechanisms resulting in a secondary immune response phenotype for these cells. It is also believed that transfer factors are released by stimulated T cells into the extracellular milieu where they bind to a transfer factor receptor molecule on the surface of nearby naive T cells. Following MHC-restricted antigen presentation, it is believed that these cells will also adopt a secondary immune response phenotype. It is also believed that transfer factors released by T cells have a role in antigen presentation which may be manifested through the specific antigen binding activity of transfer factors and facilitated through the formation of MHC product/transfer factor/antigen complexes on the surface of antigen presenting cells.

The purification strategy was based on several considerations not considered by the prior art. The defining and most well-established assay for transfer factors is an in vivo assay for delayed typed hypersensitivity. Therefore, there was a need to preserve the biological activity of the transfer factors throughout the purification process. Second, the in vivo assay for transfer activity has traditionally been performed using a single dose sample. Whereas this approach provides important qualitative information on the presence of transfer factor activity, it was necessary to develop a quantitative assay to properly monitor the purification process. Third, early experiments indicated only picomolar quantities of transfer factors were obtained from gram quantities of tissue. Furthermore, methods were sought which would yield material of sufficient quality and quantity for biochemical characterization and structural studies. In the interests of minimizing sample handling, and therefore minimizing non-specific sample loss, volatile buffers were used throughout the purification process. It was also found that conventional high pressure liquid chromatography solvents, such as trifluoroacetic acid inactivates transfer factors. It was therefore necessary to devise a new solvent system that would allow purification of the transfer factor while not affecting the biological activity.

Fourth, preliminary data indicated that even samples containing relatively large quantities of transfer factor activity absorb only small amounts of light at wavelengths over 235 nm. Thus, chromatographic solvent systems were selected which have utility at short wavelengths. The strategy that was developed is shown in FIG. 1. It should be noted that in FIG. 1, the two high performance liquid chromatography steps may be reversed, i.e., the polytypic (gel filtration) high performance liquid chromatography can be performed first and the reversed-phase high pressure liquid chromatography can be performed second. In some cases, the desired specific activity can be obtained after the affinity purification step.

Specific activity is defined in terms of transfer factor activity per absorbance unit at 214 nm. This measurement of specific activity was developed because substantial portions of the samples would have been required to make conventional protein determinations, and because absorbance of short wavelength UV light is an accepted, non-destructive means for the detection of peptides and proteins. Development of this system for relating transfer factor activity in units to protein concentration allowed specific activity to be monitored throughout the purification process.

Briefly, the isolation procedure is a method of producing substantially pure transfer factor comprising the steps of contacting a transfer factor-containing sample to an immobilized antigen to which the transfer factor binds specifically under conditions favoring binding of antigen-specific transfer factor to the antigen to form a transfer factor:antigen complex. The antigen-specific transfer factor is then separated from the complex. The antigen-specific transfer factor is then applied to a first reversed phase, high performance liquid chromatography column. The antigen-specific transfer factor is eluted from the first reversed phase, high performance liquid chromatography column and is then applied onto a second, gel filtration, high performance liquid chromatography column. The two high performance liquid chromatography column steps can be reversed. The substantially pure transfer factor is then eluted from the second high performance liquid chromatography column, the antigen-specific transfer factor having a specific activity of at least 5,000 units per absorbance unit at 214 nm.

The following specific examples will illustrate the invention as it applies to enhancing the immune response of an organism to small haptens. It will be appreciated that other examples will be apparent to those of ordinary skill in the art and that the invention is not limited to these specific illustrative examples.

EXAMPLE 1

This example explains the preparation of crude dialysates which contain transfer factor.

Following Petersen et al.[42], groups of 100–150 BALB/cByJ mice, 8–14 weeks old, which had been maintained on water and pellet food ad libitum, were "sensitized". This means that either ferritin or chicken egg albumin in aqueous solution was emulsified in equal amounts of Hank's Balanced Salt Solution (HBSS), and Freund's complete adjuvant. Each mouse received 100 µg of the sensitizing antigen in a 40 µl volume, which was injected into two sites at the base of the tail, subcutaneously. After three weeks, six mice were selected randomly and were subjected to a delayed type hypersensitivity assay. This assay involved injection of 100 µg of antigen in 25 µl of HBSS, which was injected subcutaneously into hind footpads. Contralateral footpads were injected with 25 µl of HBSS. The antigen used in the assay was the same one administered to the mice previously. The footpad thickness was measured before and 18 hours after injection, using a dial gauge micrometer. Scores were taken from the difference between these values. Previous experimental work by Petersen et al. had shown that maximal swelling occurs 18–24 hours after injection.

42Petersen et al., *J. Immunol* 126: 2480–2484 (1981)

If the subject mice had footpad swelling responses to the antigen significantly greater than the response to the diluent (p<0.05), all mice in the group were sacrificed. Spleens were removed aseptically, and single cell suspensions were prepared by gently forcing the cells through sterile 60 mesh stainless steel screens. The cells were washed three times with HBSS, an aliquot was removed, and mononuclear cells counted using trypan blue as vital exclusion dye. Overall viability was always greater than 90%. Cells were then suspended in sterile purified water in 50 ml sterile propylene centrifuge tubes, and lysed via repeated freezing in dry ice-ethanol baths and thawing in 37° C. water baths. When microscopic observation confirmed that lysis was essentially complete, the lysates were placed in dialysis bags which had previously been boiled in purified water. These bags had molecular weight cut offs of 6000–8000 Daltons. Dialysis was carried out at 4° C. against 50 volumes of sterile purified water under constant stirring for 24 hours. This was conducted twice, serially. The dialysates which resulted were pooled and lyophilized, and the lyophilized material reconstituted to $10^8$ mononuclear cell equivalents (ce)/ml, using purified sterile water. After sterilization by passage through a 0.22 µm filter, and confirmation of sterility by testing an aliquote on blood agar plates, the cells were stored at −20° C.

EXAMPLE 2

The dialysates were assayed for transfer factor activity as described by Kirkpatrick et al., the disclosure of which is incorporated by reference.[43]

43Kirkpatrick et al., *J. Immunol* 134: 1723–1727 (1985)

Volatile solvents were removed from samples by lyophilization. Samples were brought to a concentration of $10^8$ mononuclear cell equivalents per mililiter using sterile purified water as diluent. Test materials were administered to mice by intra-peritoneal injection of 1.0 ml sample per mouse. Six mice were used for each data point unless indicated otherwise. The assay for delayed-type hypersensitivity was initiated 24 hours following injection of transfer factor sample.

For purposes of quantitating recovery between purification steps, one unit of transfer factor activity was defined as the material producing a half-maximal footpad swelling response from a dose-response curve of $log_{10}$ of the mononuclear spenocyte equivalents versus the increment of footpad swelling. With the exception of the crude dialysates, the various purified preparations contained such small amounts of protein that substantial proportions of the samples would be required for conventional protein assays. For purposes of this application, the specific activity of the preparations is described in terms of the number of units of transfer factor activity per absorbance unit at 214 nm. The various volatile solvents were removed from samples through lyophilization. The samples were dissolved in purified water for absorbance measurements. These absorbance measurements were made using self-masking quartz glass microcuvettes (type 18M-S; NSG Precision Cells, Inc., Farmingdale, N.Y.) and a Gilford model 260 UV spectrophotometer (Gilford Instrument Laboratories, Inc. Oberlin, Ohio).

This assay is the protocol used for all tests of activity described herein, whenever reference is made to an "in vivo transfer factor assay".

EXAMPLE 3

This example describes affinity purification of transfer factor, following Kirkpatrick et al., which is incorporated herein by reference.[44] Immulon 2 Removawell strips were filled with antigen at a 100–200 µM concentration in a 0.05M sodium carbonate buffer, pH 9.6. Wells were incubated overnight at 4° C. in a humid chamber, followed by washing three times with a PBS-TWEEN 20 solution (0.15M PBS, pH 7.4, 0.5 ml TWEEN-20/liter). Bovine serum albumin was then added at a concentration of 100 mg/ml. The wells were incubated at room temperature for one hour to saturate remaining protein binding sites.

44Kirkpatrick et al., *J. Immunol* 135: 4027–4033 (1985)

This was washed three more times with the PBS-TWEEN solution. Then, spleen cell dialysates containing transfer factor were applied at $10^8$ mononuclear ce (cell equivalents)/ml and at a volume of 300 µl. Dialysates corresponded to the antigen that had been added previously, e.g., cell lysates from animals immunized with ferritin were used with ferritin treated strips. The strips were then incubated at 4° C., 24 hours in a humid chamber.

The wells were washed two more times with PBS-TWEEN 20, and then once more with PBS. Following this, 300 µl of acetonitrile were added, and the wells were incubated for ten minutes at room temperature. Supernatants were removed, and an amount corresponding to $2.4 \times 10^8$ ce (2.4 ml) were set aside for the in vivo transfer factor assay described above. Samples were dried under nitrogen in a 37° C. water bath. The samples for the assay were reconstituted to $10^7$ ce/ml, using purified water. The material used in further purification steps was dissolved in from 1–5 ml of 5 mM ammonium bicarbonate. The use of this material is described herein.

EXAMPLE 4

Affinity purified transfer factor was then applied to reversed phase high performance liquid chromatography. It should be noted here that use of conventional column solvents, e.g., trifluoroacetic acid results, in inactivation of the transfer factors. Therefore, a new solvent system for running the columns had to be devised to preserve transfer factor activity.

Between 10 and $30 \times 10^8$ ce were dissolved in a 0.2 to 0.5 ml volume of purified water, and this was applied to a 4.6×250 mm Vydac, 218TP54 octadecylsilane column, using 5.0 mM ammonium bicarbonate at flow rate 1.0 ml/min. Fractions were collected at 1 minute intervals, and UV data permitted detection. This was done via UV spectral data taken over 1.0 second intervals, between 203 and 280 nm, and monitoring absorbance at 214 nm.

Results not shown here demonstrated that when 5 mM ammonium bicarbonate and acetonitrile were used, with acetonitrile ranging from 0–60% of the eluate, all transfer factor activity eluted in the void volume. As a result, elution was carried out isocratically using 5 mM ammonium bicarbonate, and the unretained peak collected. Aliquots, usually containing $2.5 \times 10^8$ ces, were set aside for transfer factor in vivo transfer factor assays. The remainder was lyophilized, reconstituted using 1.0 ml of 10 mM formic acid, and retained at −20° C. for further purification by polytypic high performance liquid chromatography on gel filtration columns.

EXAMPLE 5

This example is directed to the purification of transfer factor using polytypic high performance liquid chromatography on gel filtration columns.

The manufacturer of the columns recommends an eluent ionic strength of at least 0.1M to minimize non-specific interactions between sample components and the column bed material. Optimal resolution of the transfer factor samples was achieved using a ten fold lower ionic strength than that recommended by the manufacturer.

To accomplish this, 20–30×10$^8$ ces of mononuclear cells were applied in 0.2 to 0.5 ml volumes to two 7.8×300 mm gel filtration high performance liquid chromatography columns, linked in series. This was eluted with 10 mM formic acid, pumped at a flow rate of 0.5 ml/mm. This system had a void volume of 12.2 ml and fractions were collected at 1.0 minute intervals, detection being accomplished as indicated above.

EXAMPLE 6

Comparative data were obtained by using the ion pairing agent TBAP and a 4.0×300 mm octadecylsilane column for reversed phase high performance liquid chromatography. Gradient elution in pilot experiments using 5 mM TBAP as starting solvent and 80% acetonitrile as final solvent indicated that all transfer factor eluted prior to a 25% (v/v) acetonitrile concentration. Linear gradients were performed using 5 mM TBAP/acetonitrile (92:8; v/v) as solvent "A" and 5 mM TBAP/acetonitrile (75:25; v/v) as solvent "B". Gradients were of the form: 0% B (10 minutes), 0–100% B (5 minutes) and 100% B (5.5 minutes). Flow rate was 0.5 ml/min, detection being carried out as described above.

EXAMPLE 7

A molecular weight determination was carried out using an adaptation of gel filtration high pressure liquid chromatography methodology developed by Meyerson et al.[45] Individual samples were passed through two 7.8×300 mm gel filtration high performance liquid chromatography columns linked in series, using 50 mM potassium phosphate buffer, pH 7.0 with 200 mM NaCl as eluant. Samples were dissolved either in eluant or 1.0 mM HCl, depending on solubility. Empirically determined flow rate of 0.49 ml/min was used for eluant. The void volume was 12.0 ml (24.4 min), and total permeation volume of 22.5 ml (46.0 min).
[45]Meyerson et al., *Peptides* 7: 481–489 (1986)

EXAMPLE 8

A microdialysis method was used to analyze purified transfer factor preparations. The microdialysis method was a modification of that described in Overall.[46] Spectra/por 7 dialysis tubing was cut into small squares and washed in purified water. Potential peptide binding sites were saturated by incubating rinsed dialysis membranes at 4° C. for 16 hours with 0.1% (w/v) Na$_3$N solution containing 25 µg/ml of a glutamic acid terpolymer of Mr 405, together with 25 µg/ml of peptide LWMRFA, Mr 823. Supernatant was discarded, and purified water added to the tube, followed by moderate shaking. Rinsing was repeated at least 8 times.
[46]Overall, *Anal. Biochem.* 165: 208–214 (1987)

Following this, a cap of a 1.5 ml microcentrifuge tube was punctured using the wide end of a heated Pasteur pipet. Samples for dialysis ranging from 200 to 1000 µl were placed in the tubes, and dialysis membrane pieces placed across the open end. The cap was closed, and the tube inverted and fixed, using tape to the inner wall of a dialysis chamber containing 500 ml pure water. Trapped air was removed using "u" or hook shaped tipped Pasteur pipets, covered with a small piece of tubing.

Dialysis was carried out at 4° C. under constant stirring for from 2–6 hours, depending on sample volume. Dialysate was discarded and, as needed, the above was repeated. Microcentrifuge tube was removed and centrifuged for 10 seconds in a microcentrifuge. The sample was carefully removed using a sterile tipped micropipette.

EXAMPLE 9

Dose-response studies were carried out using the splenocyte dialysates and affinity purified materials described above. In these experiments, the foot pad delayed-type hypersensitivity assay described above was carried out. Groups of 6 mice were used for each data point, and the testing was performed by injecting the antigen 24 hours after i.p. injection of the sample. Responses were taken 18 hours after this.

Figure 2A:
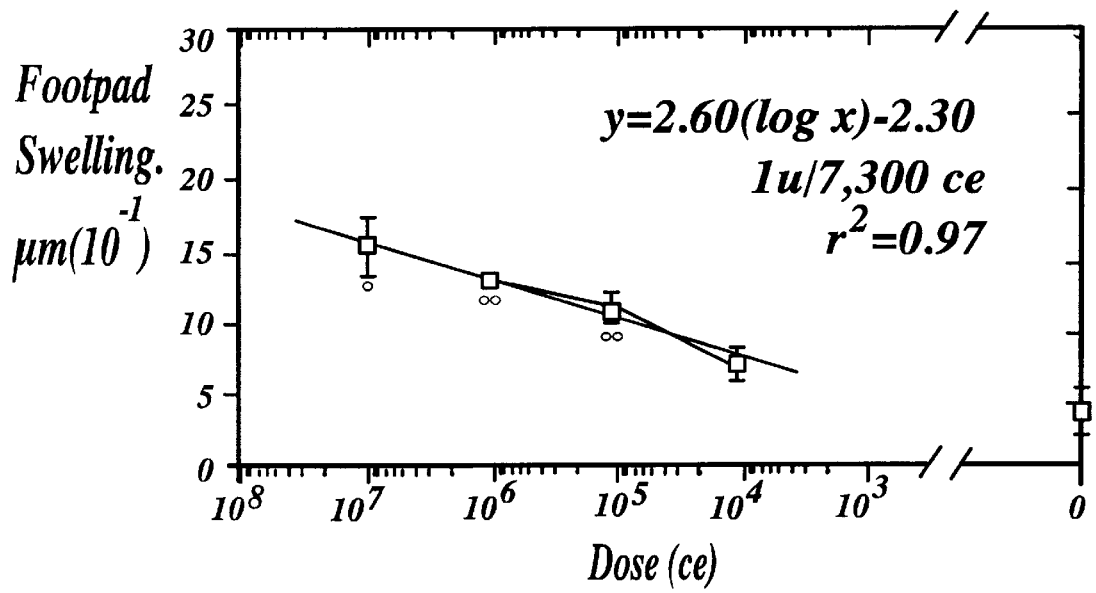
FIG. 2 shows dose-response relationships for dialysates of lysed splenocytes which contain transfer factor.
Figure 2B:
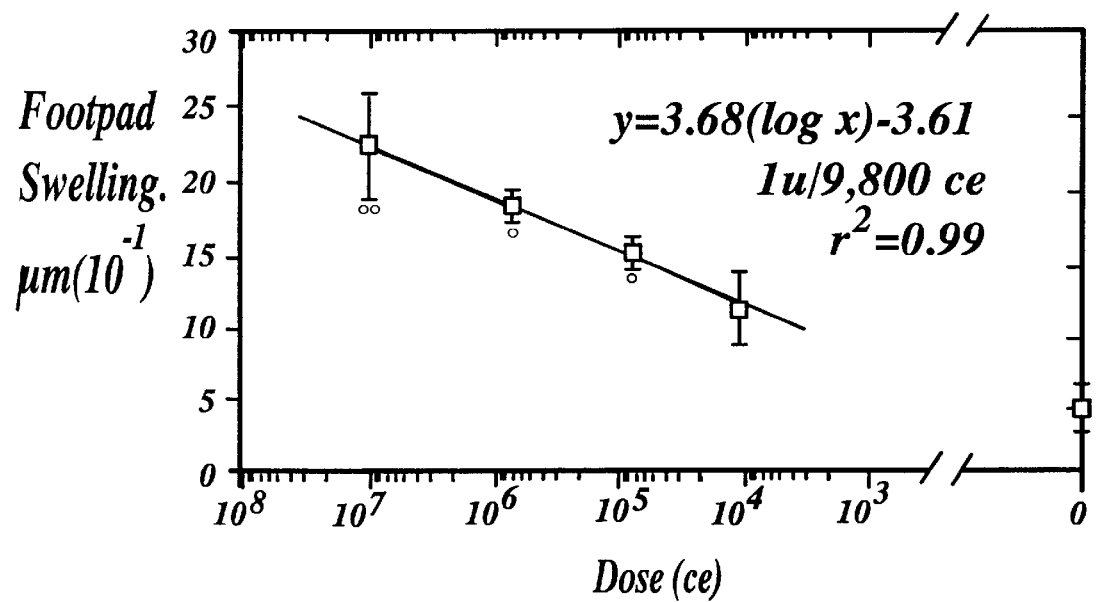

Background footpad response represents mice which received no i.p. sample. This is represented by "0 ce" in FIGS. 2 and 3. Coefficients of determination are expressed by $r^2$.

FIGS. 2 and 3 present these data. In each case, "A" represents results obtained using ovalbumin specific transfer factor, and "B" ferritin specific transfer factor.

In these data, magnitude of footpad swelling was proportional to the $\log_{10}$ of the dose when crude dialysates were used. This was previously observed by Rozzo et al. Coefficients of determination (r2) were 0.97 (FIG. 2A) and 0.99 (FIGS. 2B); therefore, the data describes the relationship well.

Figure 3A:
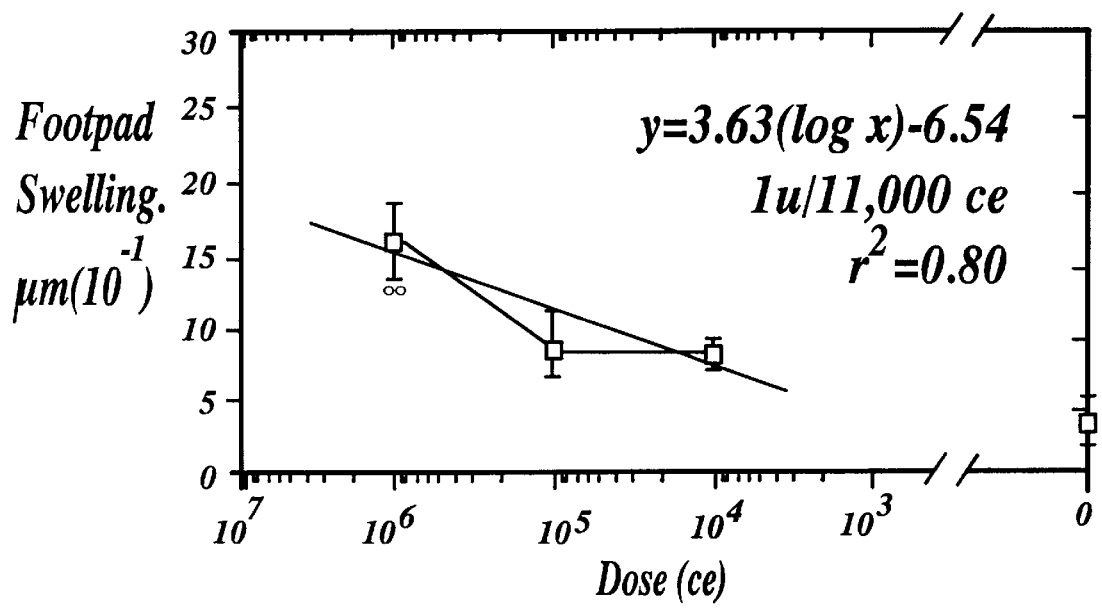
FIG. 3 shows the dose response relationship for transfer factor after affinity purification.
Figure 3B:
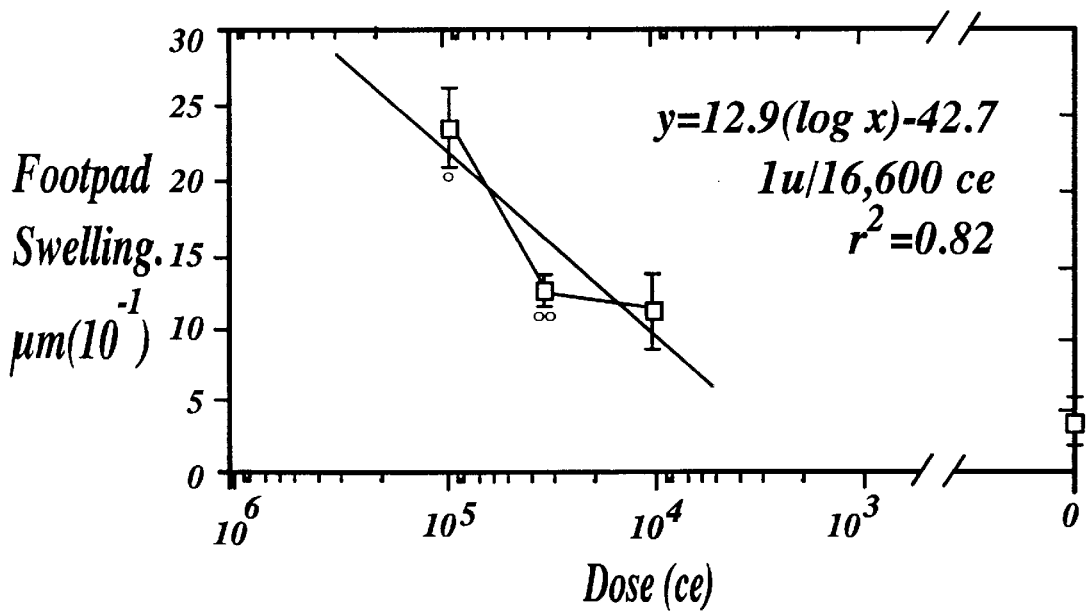

As shown in FIG. 3, the curves were similar, but the coefficients of determination were lower, being 0.80 for FIG. 3A, and 0.82 for FIG. 3B.

EXAMPLE 10

Following the purification protocols described above, yield and specific activity were calculated, also as indicated above. These results are presented in Table 1, which follows. Ovalbumin transfer factor showed a 46-fold enhancement of specific activity with a 66% yield, while ferritin transfer factor gave values of 53 fold and 59%.

In Table 1, "RPLC" refers to reversed phase liquid chromatography, and "GFC" to the polytypic high pressure liquid chromatography on gel filtration columns.

TABLE I

Yield and Specific Activities for Purified Materials[1]

| Preparation | Units TF per 10$^7$ ce | AU$_{214}$ per 10$^7$ ce | UNITS$_{TF}$ per AU$_{214}$ | Total Cell Equivalents ce (10$^{-8}$) | Total Units T.F. Activity ce (10$^{-8}$) | Individual Yield (%) | Cumulative Yield (%) |
|---|---|---|---|---|---|---|---|
| Ovalbumin Transfer Factor | | | | | | | |
| Dialysate | 1.370 | 2.770 | 495 | 484 | 66.3 | — | — |
| Aff. Purified | 910 | 0.040 | 22,800 | 470 | 42.8 | 66 | 66 |

TABLE I-continued

Yield and Specific Activities for Purified Materials[1]

| Preparation | Units TF per $10^7$ ce | $AU_{214}$ per $10^7$ ce | $UNITS_{TF}$ per $AU_{214}$ | Total Cell Equivalents ce ($10^{-8}$) | Total Units T.F. Activity ce ($10^{-8}$) | Individual Yield (%) | Cumulative Yield (%) |
|---|---|---|---|---|---|---|---|
| Fraction A[2] | 910 | 0.037 | 24,600 | 465 | 42.3 | 100 | 66 |
| Fraction AIII[3] | 770 | 0.035 | 22,000 | 463 | 35.7 | 85 | 56 |
| | | | Ferritin Transfer Factor | | | | |
| Dialysate | 1.020 | 2.340 | 436 | 145 | 14.8 | — | — |
| Aff. Purified | 600 | 0.026 | 23,100 | 143 | 8.58 | 59 | 59 |
| Fraction A[2] | 1,270 | 0.020 | 63,500 | 130 | 16.5 | 212 | 125 |
| Fraction AIII[3] | 600 | 0.080 | 33,300 | 123 | 7.38 | 47 | 50 |

[1]A unit of transfer factor activity is defined as the amount of transfer factor-containing sample (expressed in the number of mononuclear cell equivalents (ce) from which it was derived) required to produce a one-half maximal footpad swelling response. Specific activity is defined as the number of units of transfer factor activity per absorbance unit at 214 nm.
[2]Prepared using an ammonium bacarbonate-based reversed-phase high pressure liquid chromatography method.
[3]Prepared using gel filtration high pressure liquid chromatography columns in a polytypic application.

EXAMPLE 11

Figure 4:
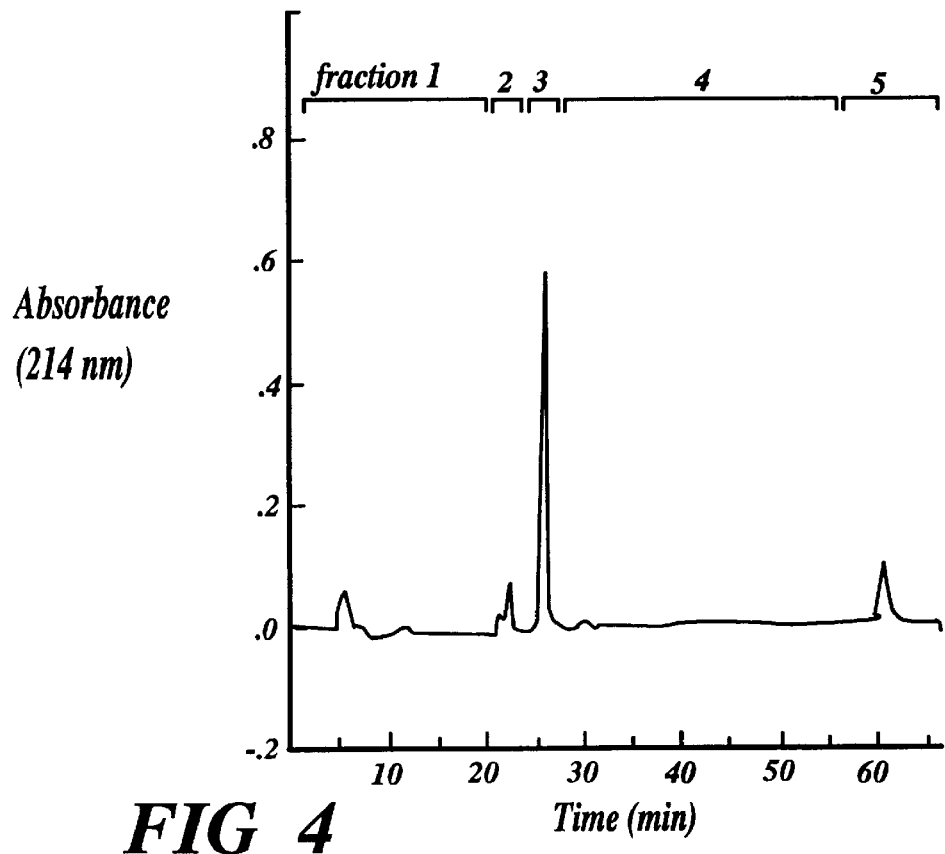
FIG. 4 shows reversed phase high pressure liquid chromatography of affinity purified ferritin specific transfer factor.

Affinity purified material, as described above, was subjected to chromatographic analysis using rplc incorporating 5 mM TBAP as ion pairing agent. "TBAP" refers to a tetrabutylammonium phosphate based solvent system. In these experiments, $43.2 \times 10^8$ ces were applied in a 400 µl volume. With reference to Example 6, fractions were analyzed. The major chromophore detected at 214 nm. (Fraction 3; time=26.4 minutes) contained transfer factor activity. Fractions 1 and 5 also showed the activity at much lower levels, as can be seen via reference to FIG. 4, showing data obtained using ferritin specific transfer factor. The activity was measured using the previously mentioned footpad assay.

These results caused focus to be placed on fraction 3.

EXAMPLE 12

Figure 5:
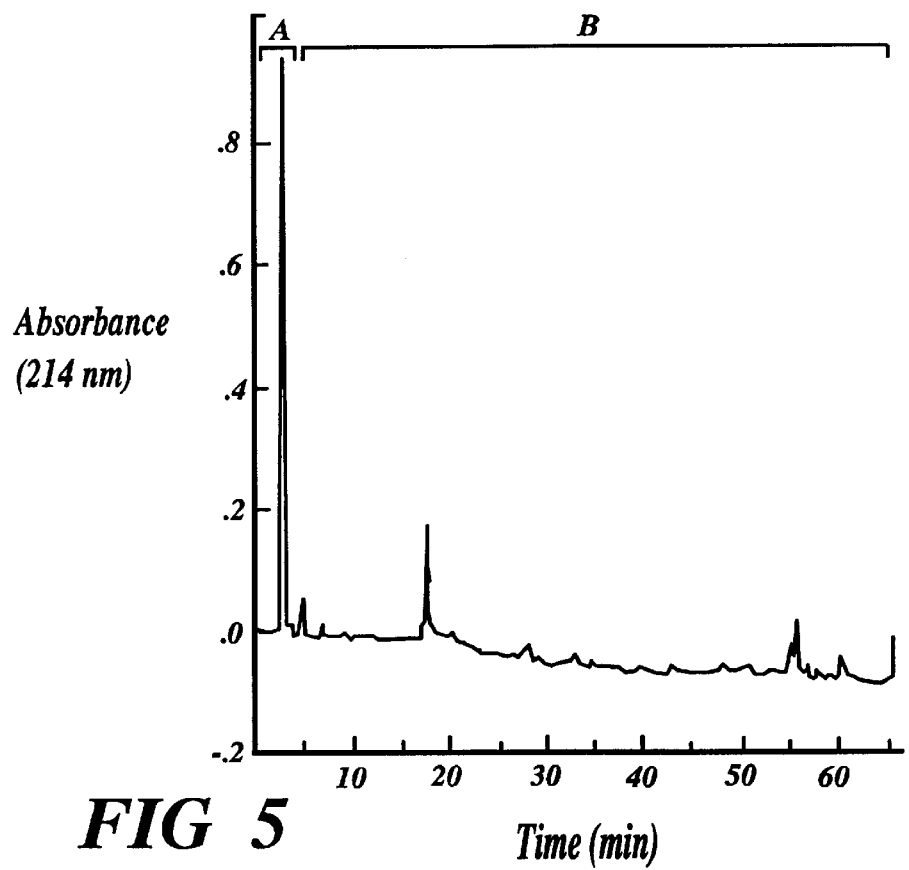
FIG. 5 shows reversed phase high pressure liquid chromatography of affinity purified ovalbumin specific transfer factor.

The elution profiles of affinity purified transfer factors were obtained, a typical one being shown in FIG. 5. To obtain this, $23.3 \times 10^8$ ce of affinity purified albumin specific transfer factors, using rplc were applied in 50 ul volumes. All transfer factor activity eluted in unretained peak (fraction A), while contaminants were retained. Transfer factor activity was measured using the above mentioned footpad assay. Fraction A showed $17.33 \pm 1.20 \times 10^{-2}$ mm (p<0.001) swelling, whereas fraction B (impurities) showed $5.5 \pm 1.61 \times 10^{-2}$ mm, with p being not significant.

EXAMPLE 13

The fraction A described above was assayed and showed only a 7% enrichment in specific activity. Yield, however, was 100%, as shown in Table I. These data were confirmed by studies which showed that rechromatography of lyophilized, reconstituted fraction A sample showed essentially the same unretained peak.

EXAMPLE 14

Fraction A type materials were obtained for ferritin specific transfer factor, just as ovalbumin specific transfer factor was obtained. This fraction showed 2.75 fold enrichment (Table I); however, there was an apparent two fold (212%) yield over affinity purified sample, and 125% yield relative to crude dialysate.

EXAMPLE 15

Figure 6A:
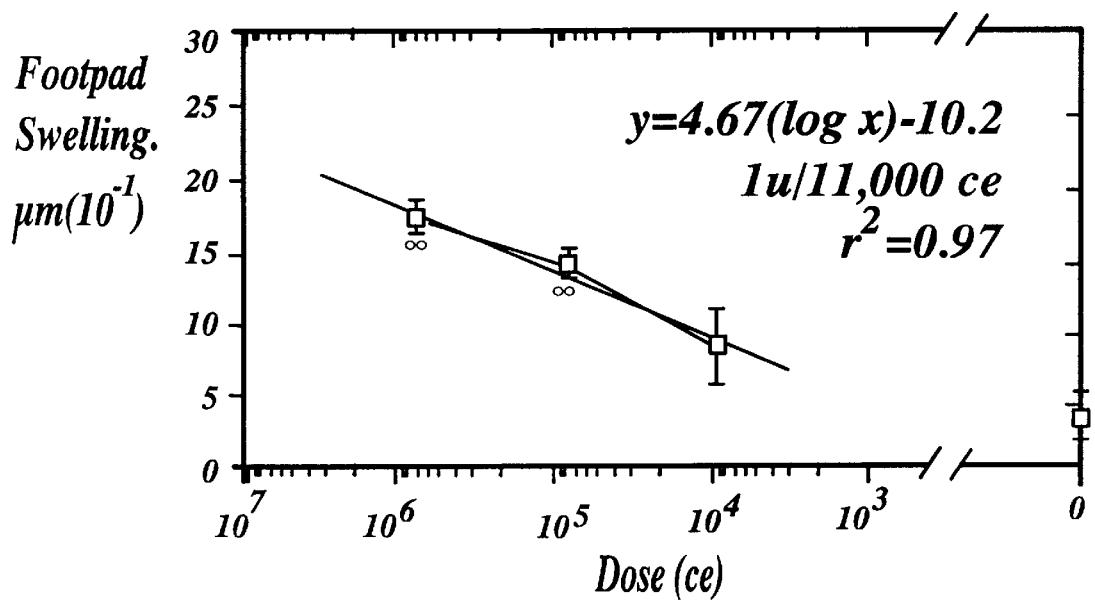
FIG. 6 shows dose response relationships for reversed phase high pressure liquid chromatography purified transfer factor.
Figure 6B:
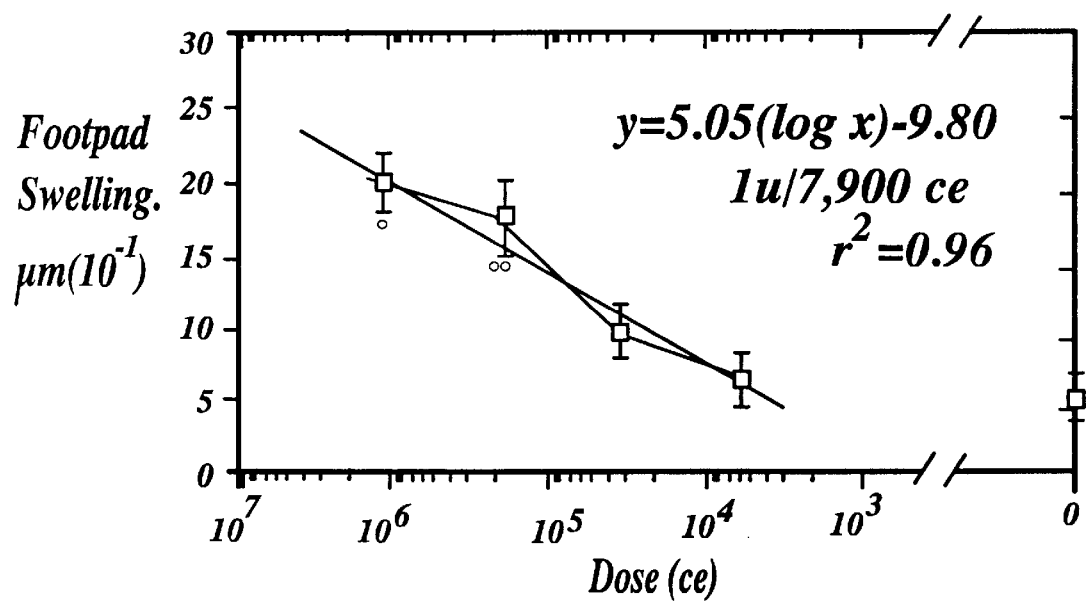

Dose response curves for the "fraction A" for both ovalbumin and ferritin specific transfer factors were obtained, as set out in Example 9. The results are depicted in FIGS. 6A and 6B (ovalbumin and ferritin, respectively). Coefficients of determination are 0.96 and 0.97, respectively.

EXAMPLE 16

Figure 7:
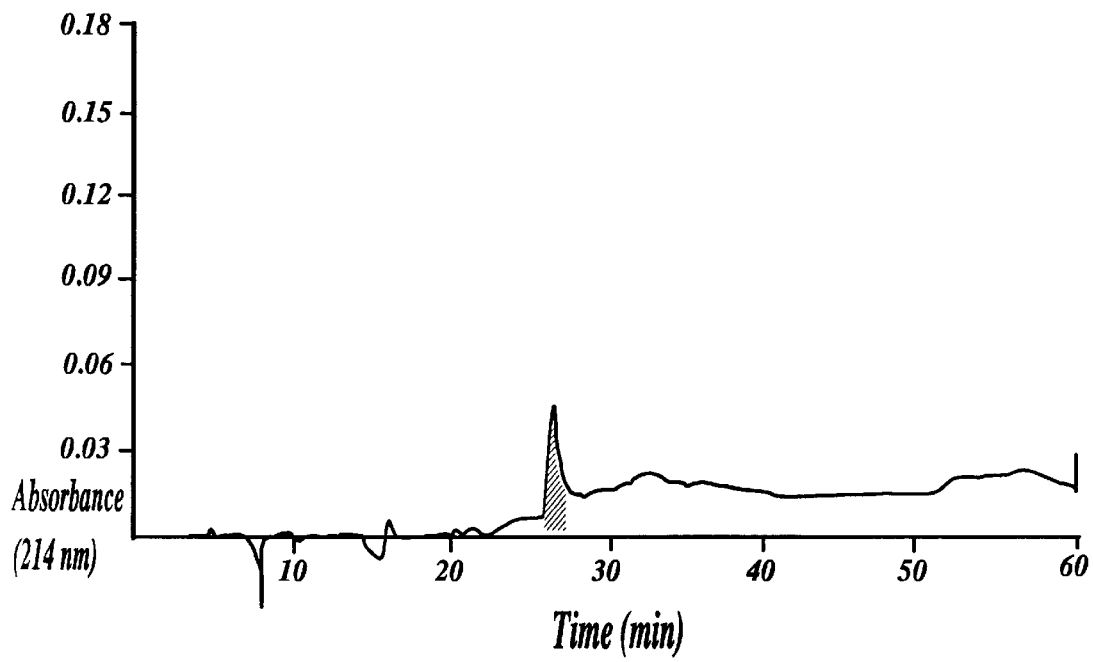
FIG. 7 depicts analysis of reversed phase high pressure liquid chromatography fractions of ferritin specific transfer factor.

Fraction A ferritin specific transfer factor material was analyzed using a TBAP system. $10.5 \times 10^8$ ce were applied to the column in a 100 µl volume. The analysis, as indicated by FIG. 7, contained four components which eluted at 4.7, 16.1, 21.3 and 26.4 minutes. Transfer factor activity was found in the last of these. After correcting for solvent baseline absorbance characteristics of the gradient, this corresponds to approximately 90% of the 214 nm absorbing material.

EXAMPLE 17

Figure 8:
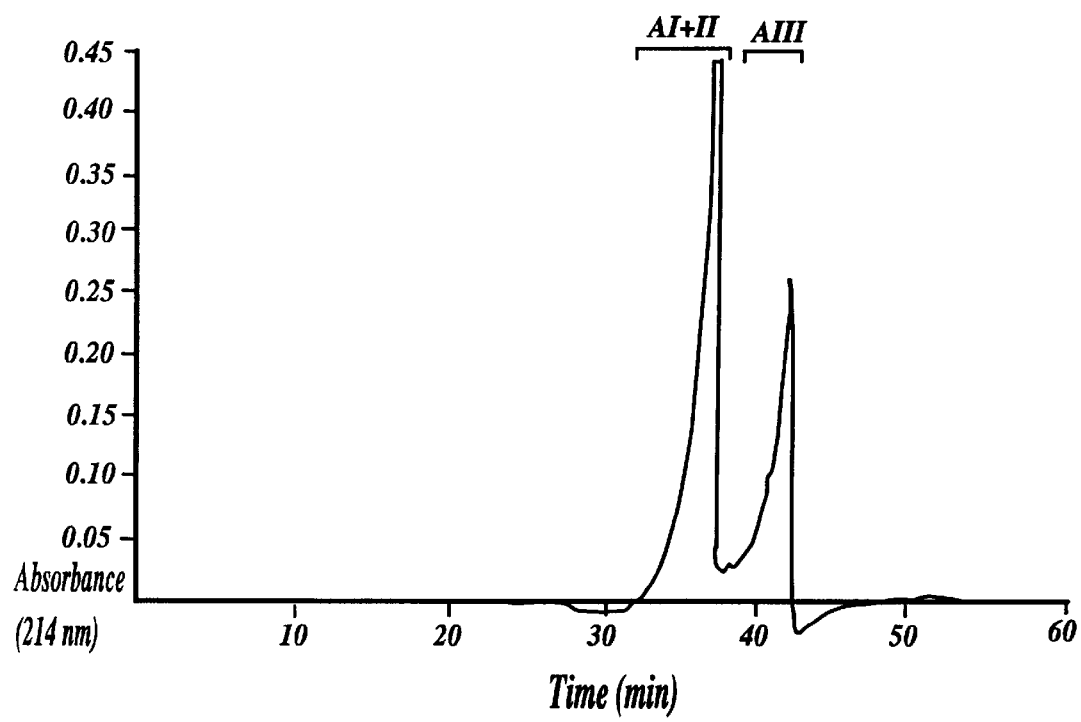
FIG. 8 presents polytypic chromatography of affinity and reversed phase high pressure liquid chromatography purified transfer factor on gel filtration high pressure liquid chromatography columns.

Fraction A material was purified further, using polytypic gel filtration high performance liquid chromatography. To do so, $25.4 \times 10^8$ ce were applied to the columns in volumes of 200 µl. The eluant was 10 mM formic acid, and an elution profile, for ferritin specific transfer factor fraction A is shown in FIG. 8. Fraction "AIII", i.e., the 3rd fraction to eluate, contained all of the transfer factor activity and was studied further.

EXAMPLE 18

Figure 9:
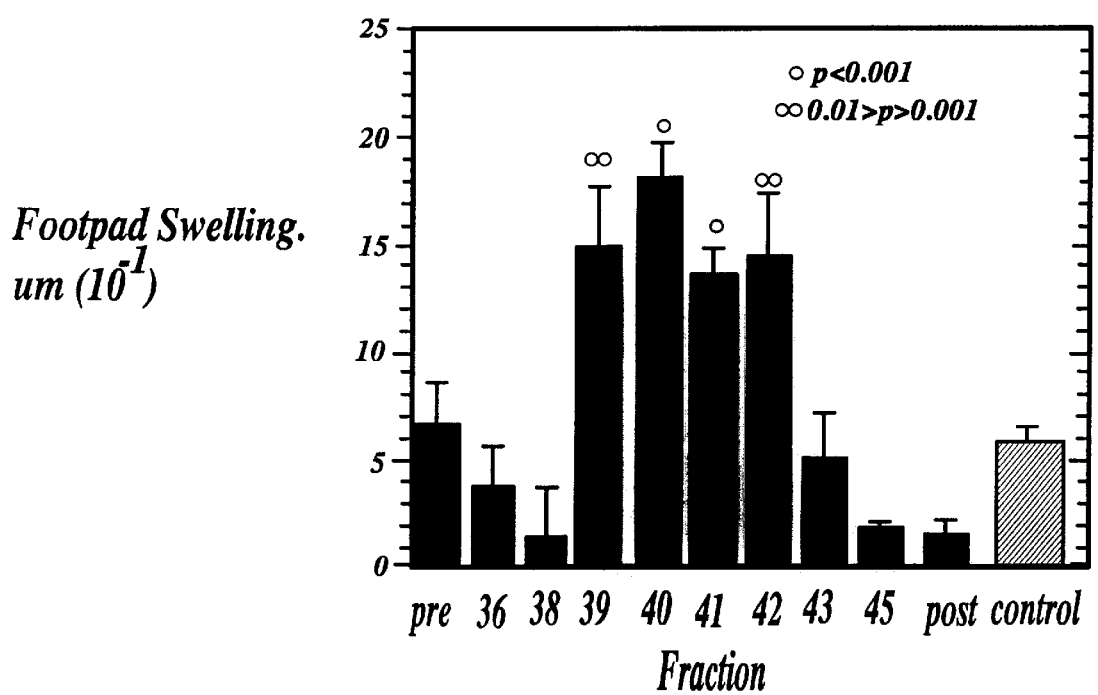
FIG. 9 presents activity data for transfer factor for ferritin, from individual fractions of polytypic gel filtration high pressure liquid chromatography.

Ferritin specific transfer factor fraction AIII from the gel filtration high performance liquid chromatography was analyzed, by neutralizing 50 µl aliquots from individual fractions with 50 mM ammonium bicarbonate, and diluted with sterile, purified water to $1.8 \times 10^6$ ce/ml. Activity was analyzed for each fraction. "Pre" fractions represent a pool of fractions 24 through 32, and "post' fractions 47–60. Transfer factor activity was found only in fractions 39–42 (FIG. 9).

EXAMPLE 19

Figure 10A:
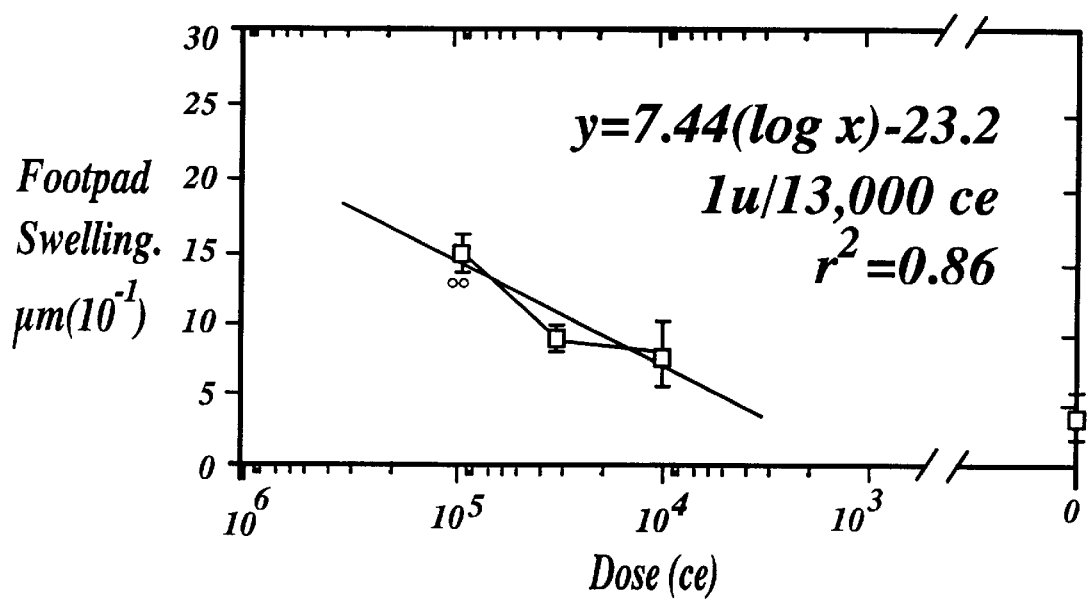
FIG. 10 shows dose response relationships for the fraction described in FIG. 8.
Figure 10B:
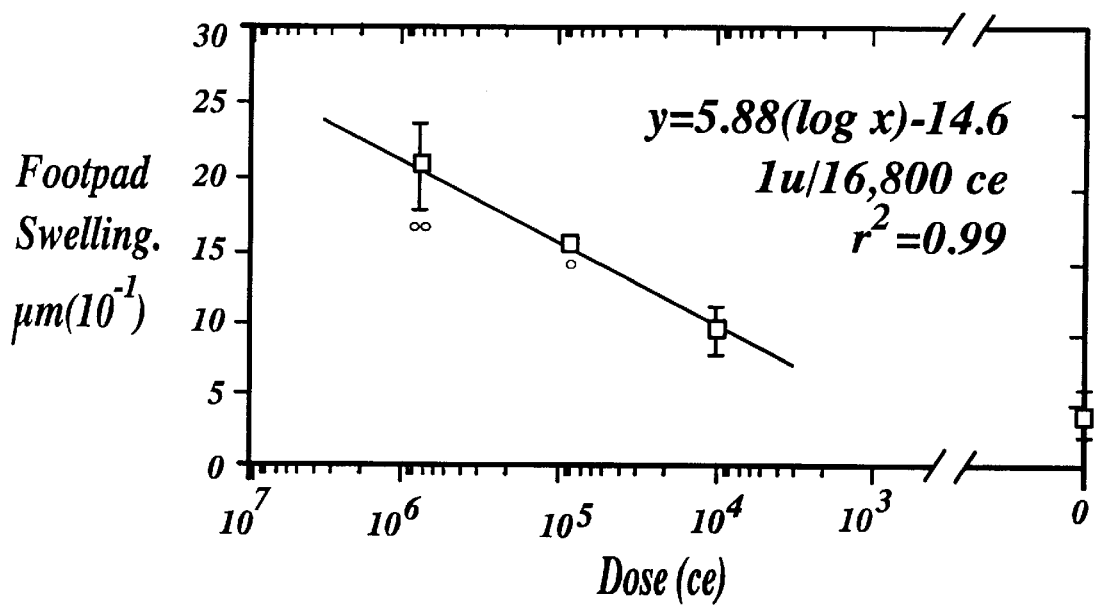

Dose response curves were derived for "Fraction AIII" materials (both types) as done in prior experiments. These results are shown in FIGS. 10A and 10B for ovalbumin and ferritin specific transfer factor, respectively. For ovalbumin, the coefficient of determination, $r^2$, was 0.86, and one unit of activity per $1.3 \times 10^4$ ce. Ferritin specific transfer factor showed $r^2$ of 0.99, and one unit per $1.68 \times 10^4$ ce. These results lead to the conclusion that spleens from mice given a single sensitizing dose of antigen and containing 0.5 to $2.0 \times 10^8$ mononuclear leukocytes would yield $3.8 \times 10^3$ to $1.5 \times 10^4$ units of transfer factor for ovalbumin. The data for ferritin would suggest $3 \times 10^3$ to $1.5 \times 10^4$ units for comparable mice, wherein the purification scheme of FIG. 1 is used.

Specific activity of the ovalbumin specific fraction was 11% less than the fraction A material, but the yield was 85%, suggesting 44 fold enrichment. With respect to the ferritin specific fraction, specific activity was 48% lower than fraction A, but 1.4 fold higher than affinity purified material, and 76 fold higher than the dialysate. Yield was 47%, giving a cumulative yield of 50%.

EXAMPLE 20

Figure 11:
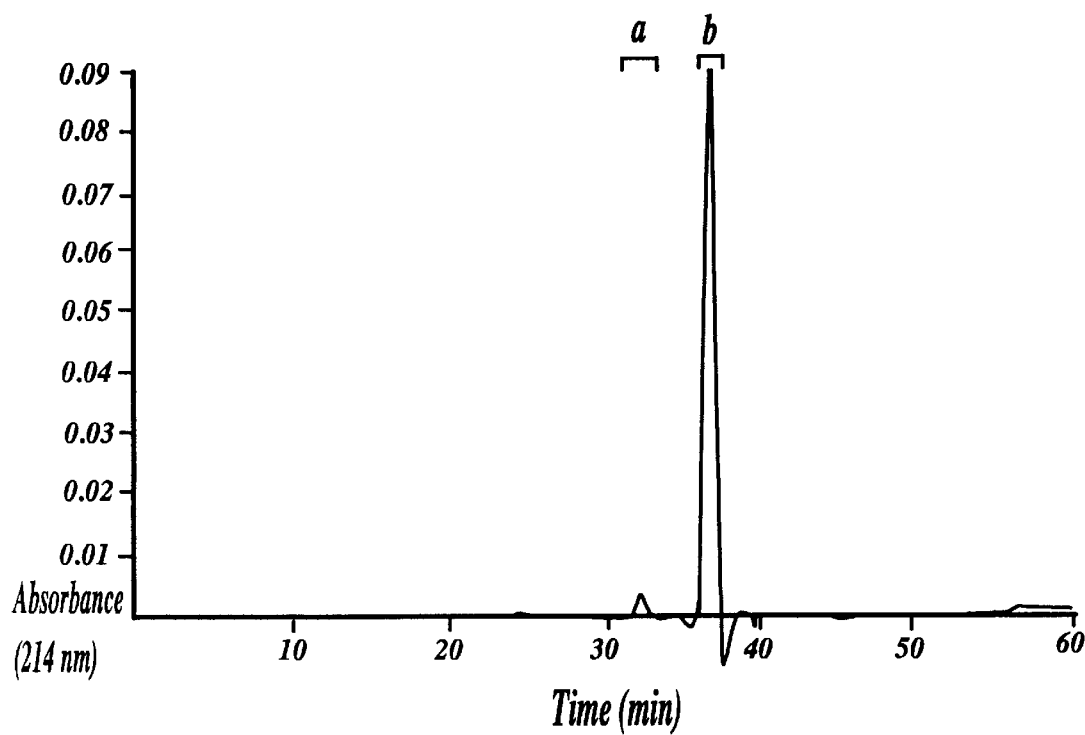
FIG. 11 presents gel filtration chromatography of a transfer factor fraction as in FIG. 8.

The gel filtration high pressure liquid chromatography method of Meyerson et al[47] was used to analyze the purity of Fraction AIII as well as to determine the molecular weight of transfer factor. An elution profile of Fraction AIII material applied to this system is shown in FIG. 11. Two peaks were obseved, with the major chromophore (peak b) representing 98% of the 214 nm-absorbing material as quantified by integrated peak area. As low recovery is frequently observed when very small quantities of proteins are subjected to conventional dialysis, therefore material from each peak was desalted by a modification of the microdialysis method reported by Overall[48] (86) prior to in vivo assay for transfer factor activity. In pilot experiments, use of this technique resulted in quantitative recovery of transfer factor activity (data not shown). After microdialysis, samples were brought to a concentration of $4 \times 10^7$ ce per ml and tested for transfer factor activity. Activity was detected only for material in peak b.

[47]Meyerson et al., supra
[48]Overall, Supra

Figure 12:
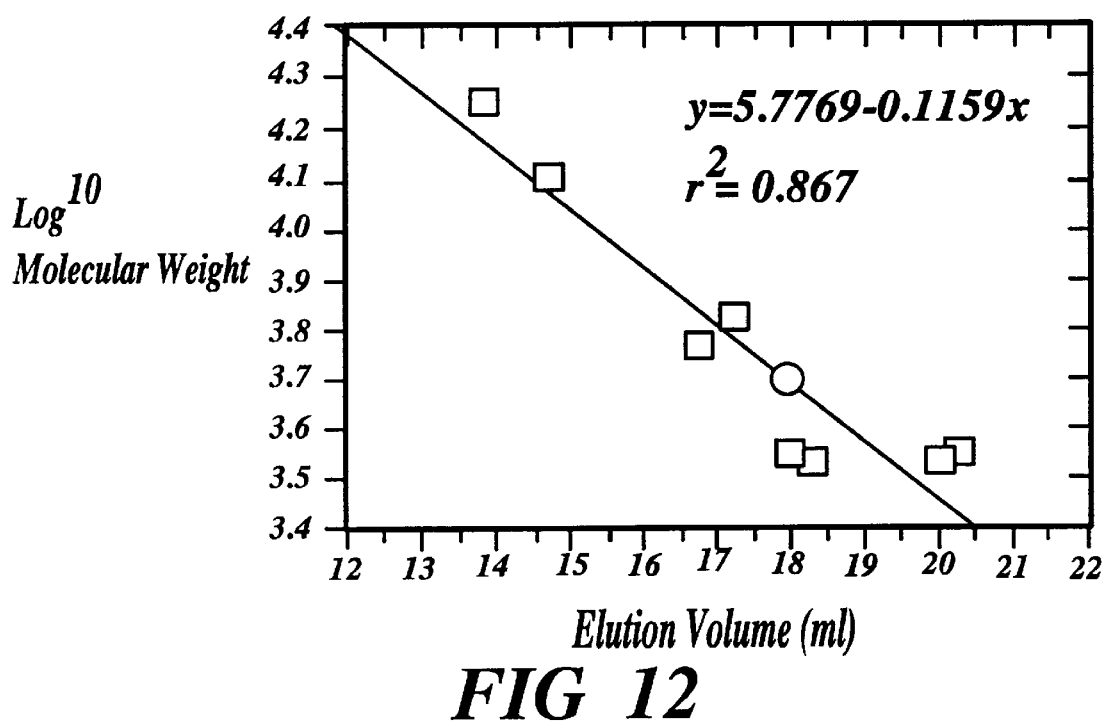
FIG. 12 shows a standard curve obtained from gel filtration chromatography of molecular weight markers.

This system was used to obtain a standard curve (of the form $\log_{10}$ molecular weight=5.7769–(0.1159)(elution volume); $r^2=0.87$; FIG. 12), the data for which were obtained by applying 8 individual molecular weight markers in separate runs. Chicken egg albumin was used to determine the void volume of the system (12.0 ml), while acetone was used to determine the total permeation volume (22.5).

The retention time of peak b was used to determine an elution volume (17.98 ml), which was in turn used to calculate a relative molecular mass for transfer factors of 4,900 Daltons. Transfer factor activity for ferritin specific material coincided with elution volume of 17.98 ml (fraction b). Footpad responses by recipients of $4 \times 10^7$ ce for fraction a were $5.83 \pm 2.31 \times 10^{-2}$ mm (p is insignificant) and $19,50 \pm 1.82 \times 10^{-2}$ mm (p<0.001) for fraction b. The peak representing fraction b contains 98% of the 214 nm absorbing material.

To determine molecular weight, the same system was used to obtain the standard curve shown in FIG. 12, for which data were obtained by using molecular weight markers in separate runs. The analysis yields an estimated molecular weight of transfer factor of about 4900 to about 5500 Daltons.

EXAMPLE 21

Spectral Data for Petrified Transfer Factors

Figure 13:
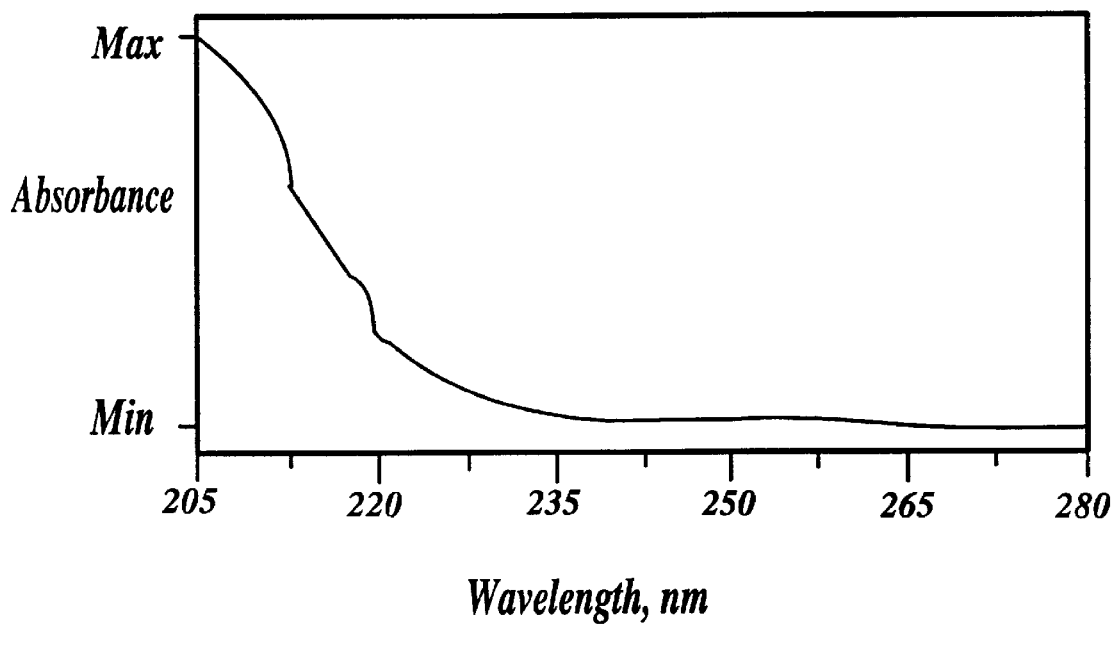
FIG. 13 shows the UV absorbance spectrum of a ferritin specific transfer factor.

An ultraviolet spectrum taken at the maximum of peak b (corrected for solvent absorbance) is shown in FIG. 13. These data, obtained from $2.5 \times 10^8$ mononuclear cell equivalents of material, show relatively little absorbance at wavelengths greater than 235 nm, including wavelengths classically used to monitor transfer factor purifications, such as 254 nm, 260 nm, and 280 nm. In fact, transfer factors have approximately 100-fold greater absorbance at 214 nm than at 254 or 280 nm. Thus, chromatography solvents which permit the use of low wavelengths, such as 214 nm, appear to provide substantial benefit in the sensitivity of transfer factor detection when monitoring chromatography using ultraviolet spectrophotometers.

EXAMPLE 22

Figure 14:
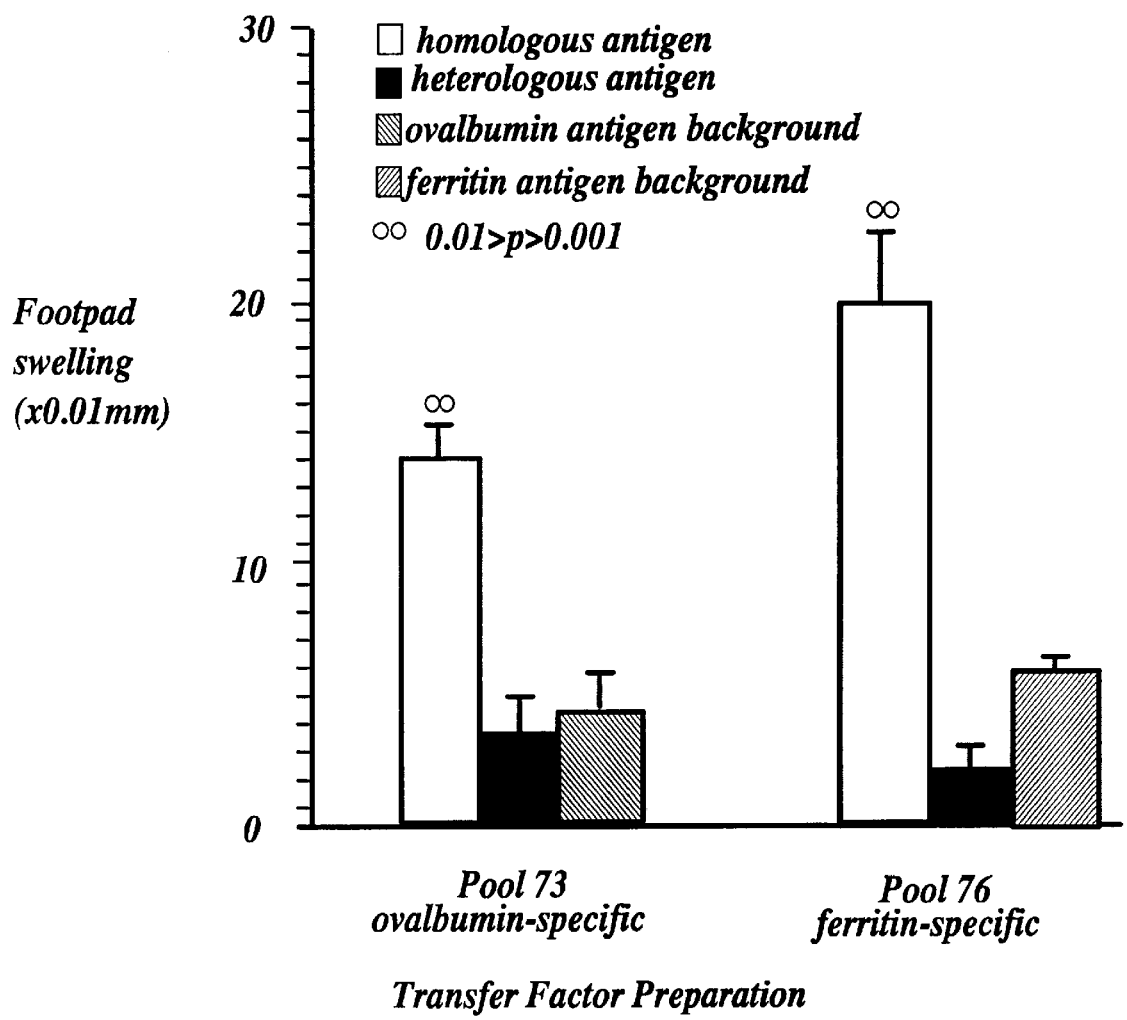
FIG. 14 depicts antigen specificity for highly purified transfer factor.

Antigen specificity of the purified AIII fraction transfer factors was studied. Mice were injected with a transfer factor preparation produced in response to one of either ovalbumin or ferritin ($10^6$ ce in 1.0 ml) followed by challenge 24 hours later with ovalbumin and ferritin. Neither preparation induced response to the heterologous antigen, but both showed the delayed hypersensitivity reaction with the homologous material indicating that the transfer factor retained antigen specificity (FIG. 14).

The transfer factor-containing dialysates described herein showed very similar specific activity (ovalbumin: 495 units at 214 nm; ferritin: 436 units at 214 nm), indicating extremely potent preparations. The data of Table 1 suggest that the spleen of one sensitized mouse, containing about $10^8$ mononuclear leukocytes, produces enough transfer factor to transfer significant delayed type hypersensitivity to at least 1000, and perhaps as many as 10,000 unsensitized recipients.

The affinity purification step, i.e., where transfer factor is reacted with its antigen, causes a loss of about 40% of transfer factor activity, but enhances specified activity by about 50-fold. Thus the purified transfer factor is extremely specific and very active.

Affinity purified transfer factor, when used in an $NH_4HCO_3$ based system, was eluted in void volume eluate, indicating the highly polar nature of the material. Data obtained for affinity purified ovalbumin specific transfer factor shows a slight increase in specific activity, and no loss of active material. The ferritin specific transfer factor gave less predictable results. The 2.75 fold increase in specific activity, taken with an apparent yield of 213%, coupled with decrease in ultraviolet absorbency, may suggest, inter alia, that an inhibitor of the transfer factor was removed. Indeed, Rozzo et al., Borkowsky et al., and Gottlieb, suggest existence of such factors.[49,50,51]

[49]Rozzo et al., Cell Imnunol. 115 130–145(1988)
[50]Borkowsky et al. in Kirkpatrick et al., ed., Immunobiology of Transfer Factor pg. 91–115 (Academic Press, 1983)
[51]Gottlieb, U.S. Pat. Nos. 4,616,079 and 4,468,379

It has been noted that earlier work postulated an oligonucleotide residue as part of the transfer factor molecule. While it is possible that the described process removed this residue, it would not account for the absence of significant 280 nm absorbance, nor would it account for the retention of biological activity. Thus, it appears that antigen specific transfer factors are peptide molecules having a molecular weight of from about 4900 to about 5000 Daltons. These transfer factors are produced in sensitized animals in extremely small, but extremely potent amounts.

EXAMPLE 23

Amino Acid Composition Analysis of Purified Transfer Factor

Purified transfer factors were analyzed to acquire information on the characteristics and properties of these molecules. Samples of Fractions 111 (from polytypic chromatography on Sephadex G-10) and Fractions AIII (from polytypic high performance liquid chromatography) were used for this purpose. Whenever possible, nondestructive methods requiring a minimal amount of sample handling and providing high sensitivity were applied. This was important due to the small physical quantity of material available and the need, in some cases, to preserve biological activity.

Amino acid composition analysis, reduction and alkylation followed by chromatographic analysis and mass spectroscopy, gel filtration high pressure liquid chromatography, SDS-polyacrylamide gel electrophoresis, and ultraviolet spectral analysis were performed to examine the purity and molecular characteristics of transfer factors. The antigen specificity of responses by recipients of purified transfer factors was studied as well.

Several strategies were used in efforts to obtain primary structure information. This was followed by a series of peptide mapping experiments using cyanogen bromide, trypsin or V8 protease to effect cleavage, followed by microbore high performance liquid chromatography. Amino acid sequence analysis was performed on the products of these experiments.

A sample of ferritin-specific Fraction III material comprised of a corrected value of $5.3 \times 10^8$ ce was subjected to amino acid composition analysis. The results are shown in Table II. The results are consistent with a proteinaceous nature for transfer factors, consisting of 65% polar amino acids. The data suggest that approximately 0.5 pmol of transfer factor is obtained from $10^8$ mononuclear cells.

The data were transformed to mole fraction values through normalization to the molar content of phenylalanine. Based on mole fraction values, a molecular weight of approximately 5,500 Daltons is predicted for transfer factors.

Potency of purified transfer factors. Since approximately 6,000 units of ferritin transfer factor activity are obtained from $1 \times 10^8$ mononuclear splenocytes (Table II), and approximately 0.5 pmol of transfer factors are obtained from $10^8$ ce, the results suggest quantities of transfer factor on the order of $10^{-16}$ moles are sufficient to induce significant sensitivity for expression of DTH responsiveness. The results underscore the high biological potency of transfer factors.

TABLE II

Amino Acid Composition Analysis of a Ferritin Tranfer Factor-containing Fraction III

| Amino Acid | Quantity (pmol) | No. of Residues[1] | Contribution to molecular mass |
|---|---|---|---|
| Asx | 2.3 | 1 | 133 |
| Glx | 10.7 | 3 | 440 |
| S | 22.0 | 6 | 522 |
| G | 44.4 | 12 | 685 |
| H | 5.8 | 2 | 274 |
| R | 7.5 | 2 | 312 |
| T | 13.8 | 4 | 404 |
| A | 19.0 | 5 | 355 |
| P | 5.89 | 2 | 194 |
| Y | 10.4 | 3 | 490 |
| V | 7.9 | 2 | 198 |
| M | 8.8 | 2 | 262 |
| I | 5.4 | 2 | 226 |
| L | 17.2 | 5 | 566 |
| F | 3.6 | 1 | 147 |
| K | 6.7 | 2 | 256 |
| Totals[2] | 191.3 | 54 | 5428[3] |

[1]Data was normalized to phenylalanine.
[2]W and C are destroyed during hydrolysis and are not included.
[3]Adjusted for 1 mol water for non-peptidyl residues.

EXAMPLE 24

Chromatographic Analysis of Reduced and Alkylated Transfer Factor

Figure 15A:
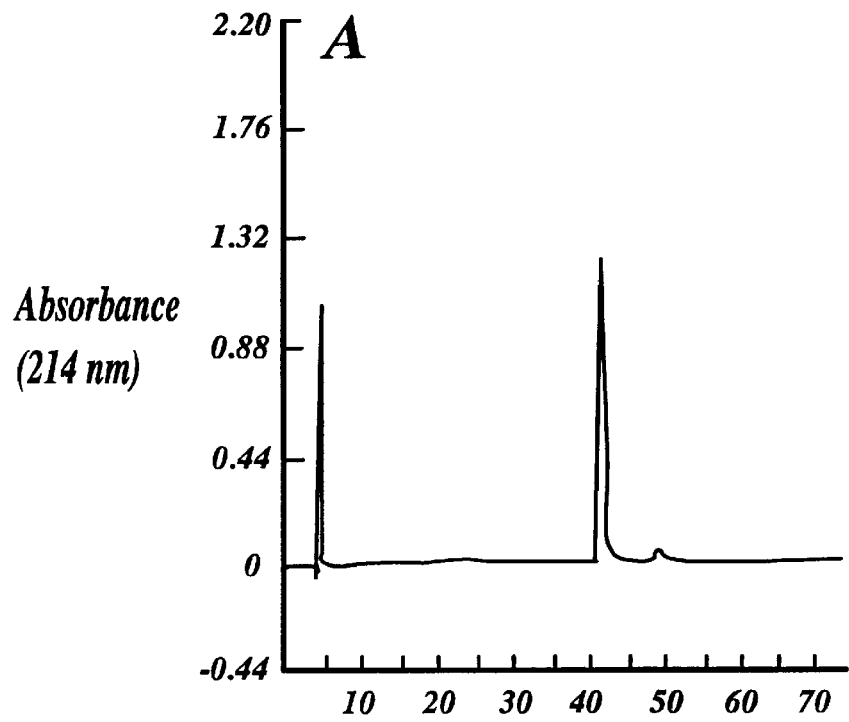
FIG. 15A shows the elution profile from a reduction and alkylation blank sample.
Figure 15B:
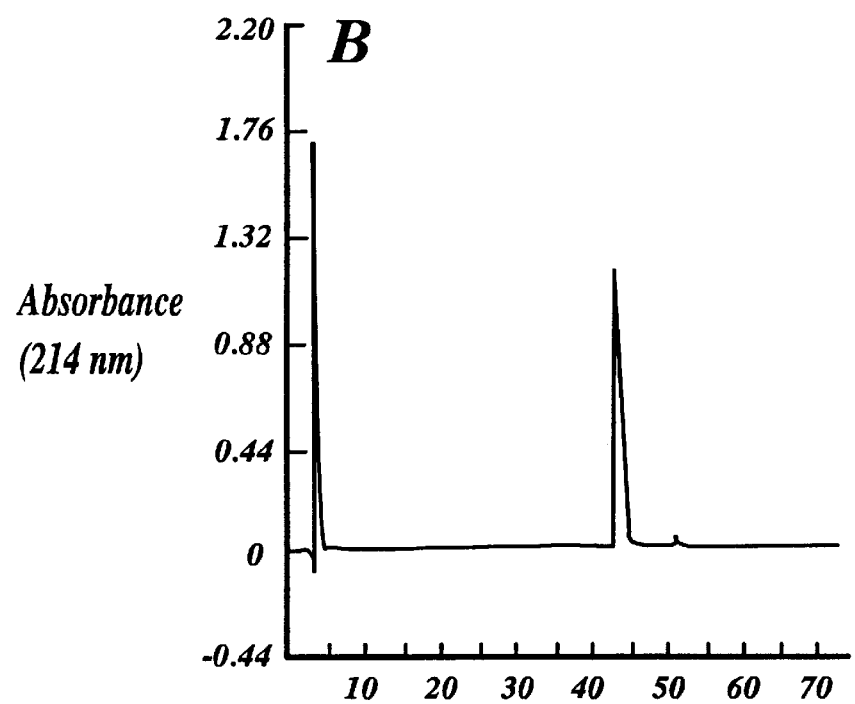
FIG. 15B shows the elution profile from a reduction and alkylation sample of transfer factor.

Fraction III ferritin-specific transfer factor was reduced and alkylated using dithiothreitol and 4-vinylpyridine, respectively, to obtain structural information. The reduced and alkylated sample was applied to an high performance liquid chromatography column containing an octadecylsilane matrix. Elution was accomplished using 5.0 mM ammonium bicarbonate as starting solvent and incorporating a linear gradient from 0 to 60% acetonitrile. FIG. 15A shows the elution profile from a reduction and alkylation blank sample, whereas FIG. 15B shows that of a reduced and alkylated Fraction III transfer factor. The unretained peak was significantly larger for the reduced and alkylated Fraction III than for the blank sample. There were no other apparent differences between the two chromatograms.

The elution of reduced and alkylated Fraction III in the unretained fraction from the ammonium bicarbonate-based reversed-phase high performance liquid chromatography system (FIG. 15B) is consistent with a lack, or small increase, in hydrophobicity.

Figure 16A:
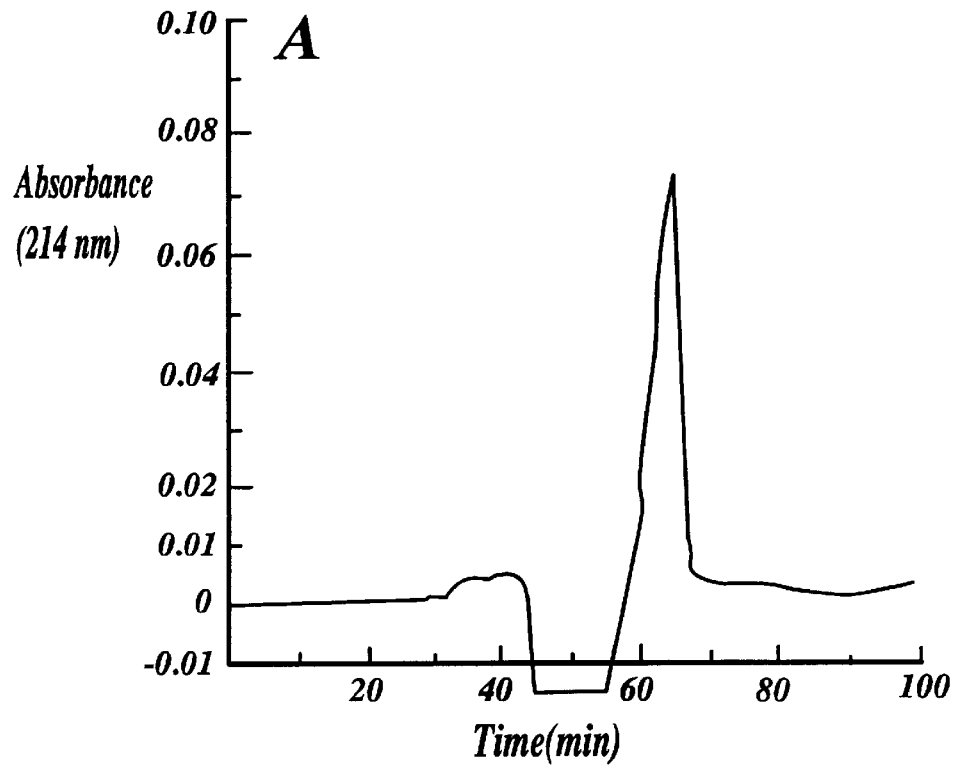
FIG. 16A shows a Sephadex G10 elution profile for control sample
Figure 16B:
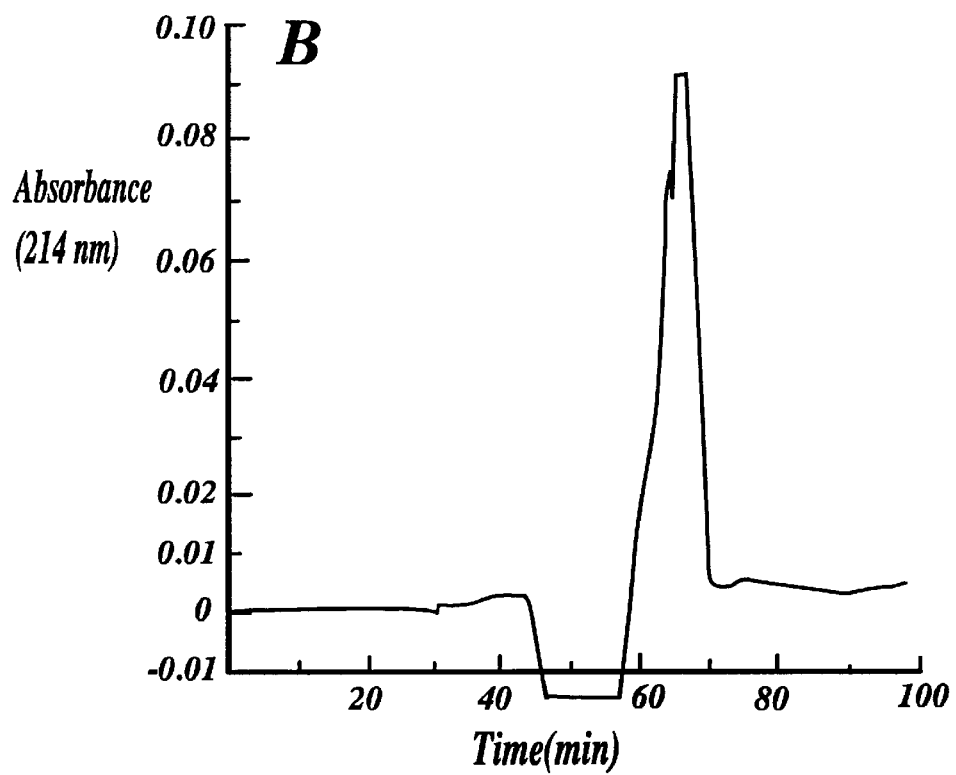
FIG. 16B shows a Sephadex G10 elution profile for Fraction III transfer factor.

The unretained peaks were collected and applied individually to the Sephadex G10 chromatography system. FIGS. 16A and 16B show the elution profiles for the control and Fraction III samples, respectively. A single unique peak was observed for the experimental sample (tR=67.60 min.). The application of the unretained fraction to the Sephadex G-10 system resulted in the appearance of a single, retained peak (FIG. 16B) relative to the blank (FIG. 16A). There appears to be a shift in the retention time for the reduced and alkylated Fraction III relative to native Fraction III.

EXAMPLE 25

SDS-Polyacrylamide Gel Electrophoresis Analysis of Purified Transfer Factors

SDS-polyacrylamide gel electrophoresis analysis of Fraction AIII materials was performed under non-reducing conditions. The results, shown in FIG. 17, support those observed using analysis by gel filtration chromatography. A single band was observed for each preparation following overdevelopment using silver staining. Both preparations produced bands which were "negatively" stained and had identical migration distances into the separating gel, although the band for ovalbumin-specific transfer factor was more prominent than that for ferritin-specific transfer factor. The apparent relative paucity of amino acids capable of reducing the silver from the ionic to the metallic state induced us to subsequently stain the gel using Coomassie Blue R-350. This resulted in development of a positive image surrounded by a clear zone for ovalbumin-specific transfer factor, but some decrease in the band/background contrast for the less-prominent ferritin-specific transfer factor band. The results are indicative of a relative molecular mass of 5,400 Daltons for both transfer factors and indicate a high degree of purity for each preparation.

EXAMPLE 26

Peptide Mapping of Transfer Factors and Purification of Cleavage Fragments

Peptide mapping for transfer factors was done using CNBr to cleave transfer factors. Either ferritin-specific or ovalbumin-specific Fraction AIII transfer factor was dissolved in acidic solution and CNBr was added. Following incubation, the reaction mixtures were lyophilized, reconstituted, and applied to reversed phase microbore high performance liquid chromatography. A linear gradient from 0.1% TFA in water to 50% acetonitrile in water was used for this purpose. No significant unique peaks were observed in experimental samples relative to the blank.

Figure 18A:
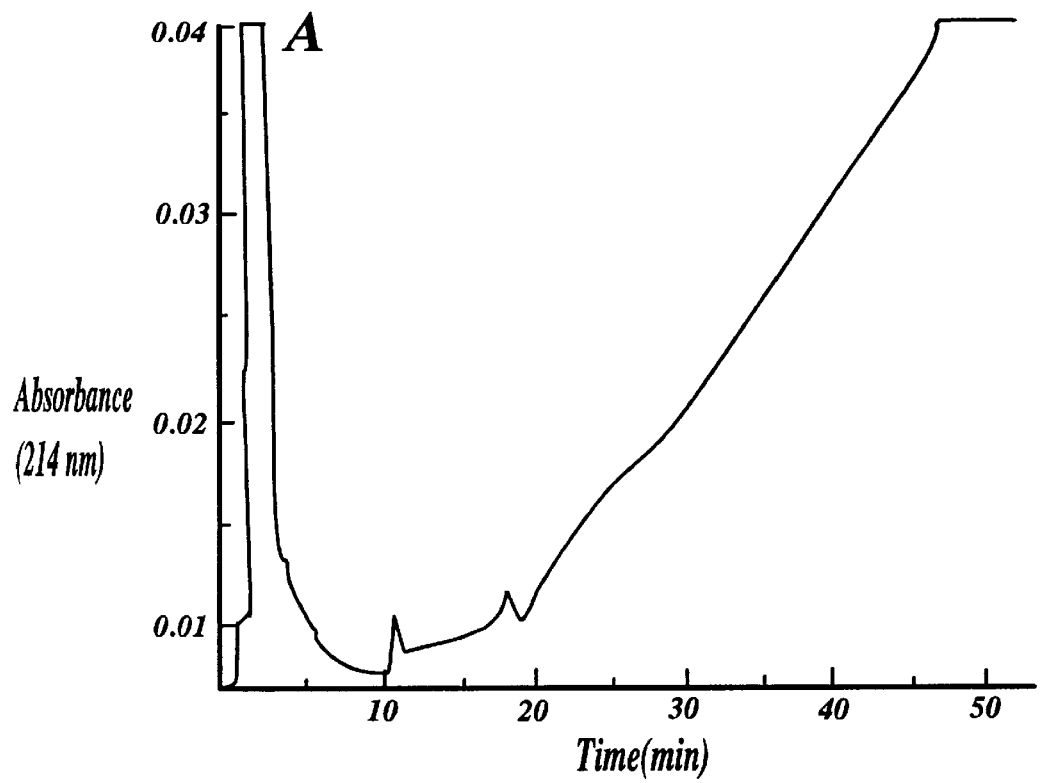
FIG. 18A is the control elution profile for the trypsin digestion of transfer factor.
Figure 18B:
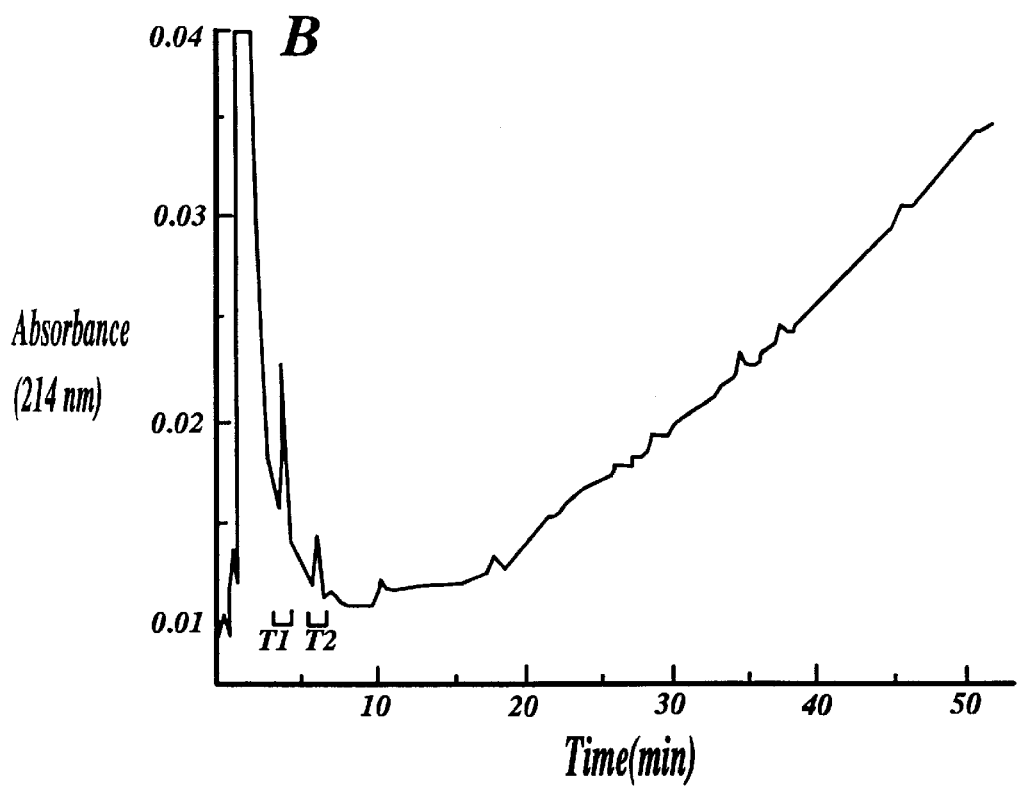
FIG. 18B shows elution profiles for Fraction AIII ferritin-specific transfer factor after trypsin digestion.

Fraction AIII ferritin-specific transfer factor was incubated in the presence of trypsin in order to perform peptide mapping. Elution profiles from microbore reversed phase high performance liquid chromatography of the reaction mixtures are shown in FIG. 23. Two unique peaks were observed for the transfer factor containing sample (FIG. 18B) relative to the control sample (FIG. 18A). No amino acid sequence data was obtained from materials from either of these peaks.

Either ferritin-specific or ovalbumin-specific Fraction AIII transfer factors, or chromatographic effluent control samples, were dissolved in a solution of ammonium bicarbonate and sodium dodecyl sulfate. V8 protease was added to these solutions, and the solutions were incubated for 18 h. Following incubation the samples were applied directly to a 1.0×100 mm reversed-phase microbore high performance liquid chromatography column containing an octadecylsilane packing. Elution was performed using a linear gradient of 5 mM ammonium bicarbonate containing 0.01% (W/v) SDS as starting solvent and an acetonitrile/5 mM ammonium bicarbonate solution (60:40;V/v) containing 0.01% (W/v) SDS as final solvent.

Figure 19A:
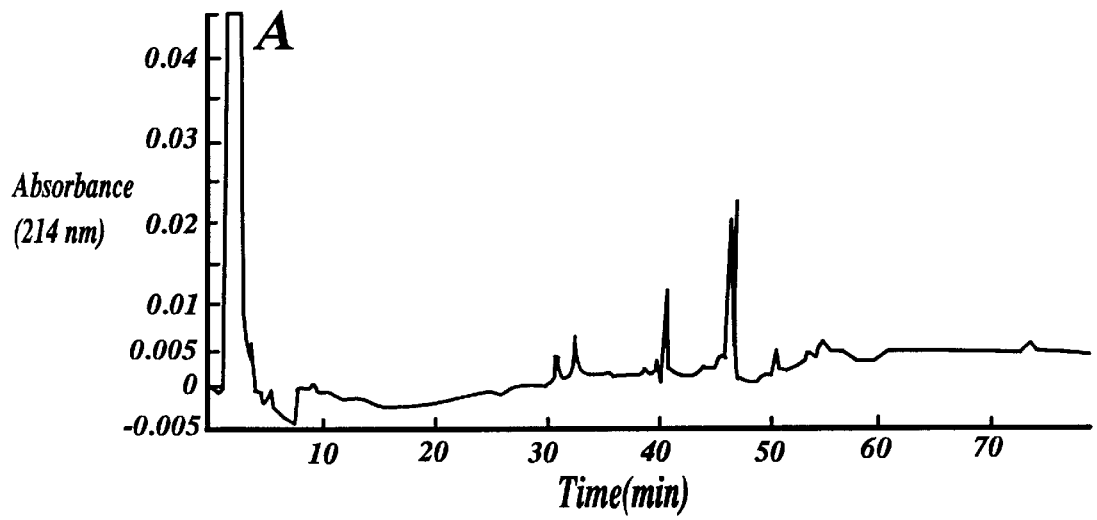
FIG. 19A is the control elution profile of transfer factor digested with V8 protease.
Figure 19B:
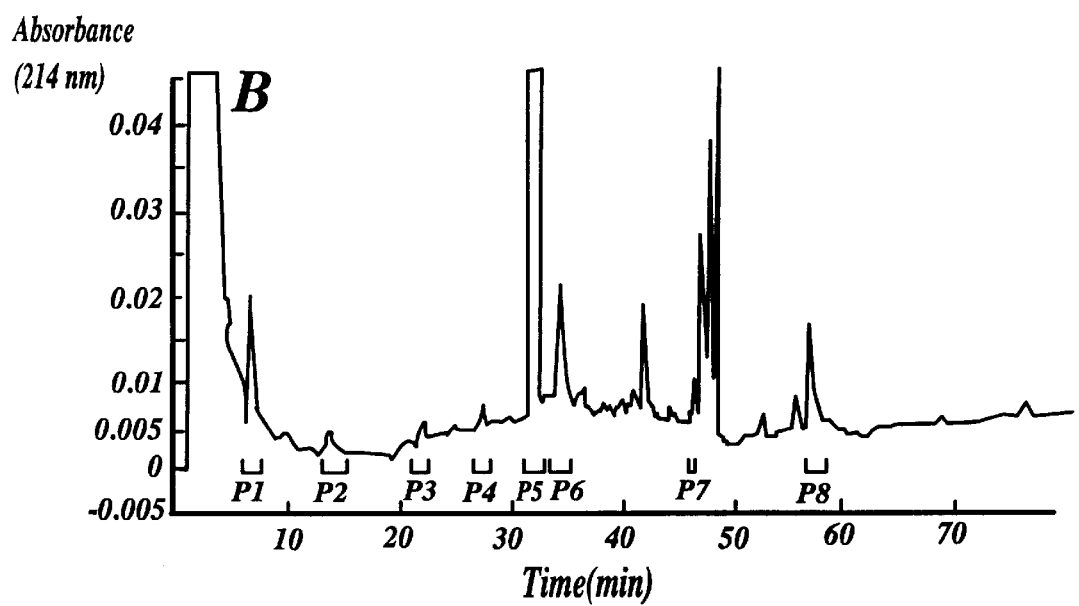
FIG. 19B is the elution profile of chicken egg albumin-specific transfer factor digested with V8 protease.
Figure 19C:
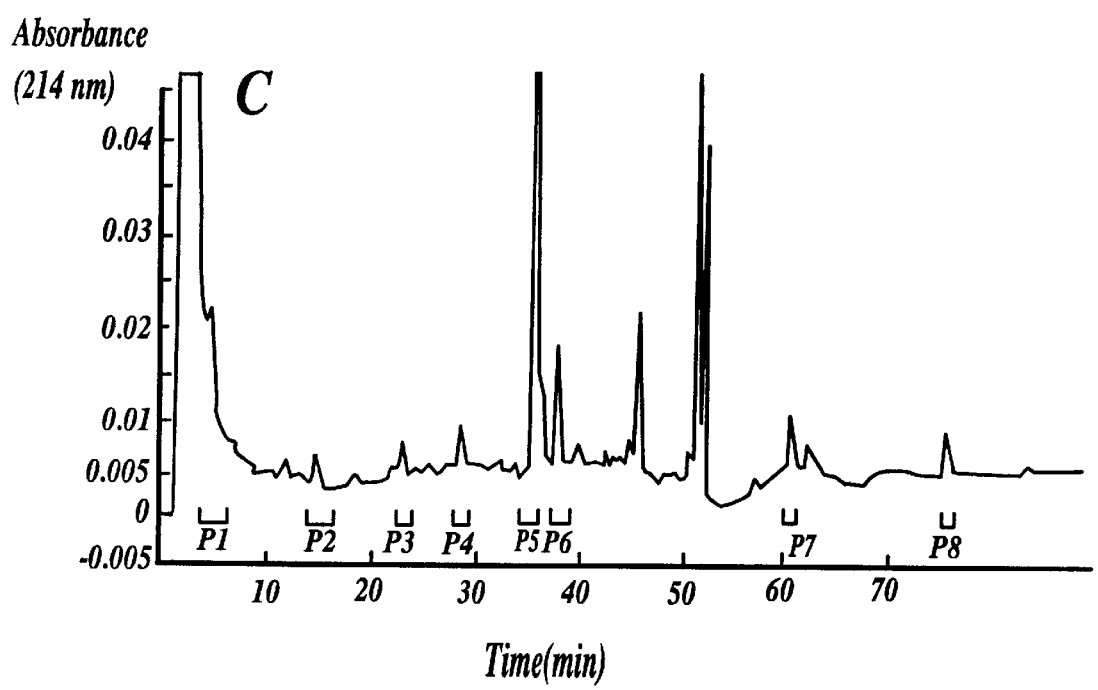
FIG. 19C is the elution profile of ferritin-specific transfer factor digested with V8 protease.

Elution profiles obtained from these experiments are shown in FIG. 19. V8 protease digests of 3 effluent controls for ferritin-specific transfer factor and 2 effluent controls for ovalbumin-specific transfer factor were analyzed using microbore high performance liquid chromatography. Essentially identical results were obtained for all five control samples. Eight transfer factor-derived peaks were observed for a chicken egg albumin-specific transfer factor digest (FIG. 19B) and ferritin-specific transfer factor digest (FIG. 19C) when compared to effluent controls (FIG. 19A). Comparing the transfer factor elution profiles to one another, three peaks were common to both preparations while 5 others were not (Table III). Of the 5 peaks, 4 appeared to have distinct, but similar, retention times, and appeared to be similar in their relative positions within each chromatogram. Each preparation produced one peak which appeared completely unrelated in its retention characteristics compared to any in the other preparation.

TABLE III

Retention Times for V8 Protease
Digests of Purified Transfer Fragments

| Peak Designation | Retention Time (min) | Peak Designation | Retention Time (min) |
|---|---|---|---|
| ovalbumin-specific transfer factor Fraction AIII | | | |
| p1 | 7.0[4] | p5 | 30.6[5] |
| p2 | 13.9[1] | p6 | 33.3[6] |
| p3 | 21.6[2] | p7 | 44.9[8] |
| p4 | 26.6[3] | p8 | 55.3[7] |
| ferritin-specific transfer factor Fraction AIII | | | |
| p1 | 4.6[4] | p5 | 32.2[5] |
| p2 | 13.6[1] | p6 | 34.1[6] |
| p3 | 21.0[2] | P7 | 53.7[7] |
| p4 | 26.0[3] | p8 | 67.0[9] |

[1,2,3]common peaks
[4,5,6,7]potentially-related peaks having similar, but distinct, chromatographic mobility
[8,9]peaks having unique chromatographic motility As has been shown, the prior art molecules consisting of peptide and oligonucleotide have been implicated in treatment of many pathological conditions. It has been shown herein that the purified proteinaceous transfer factor does transfer the delayed type hypersensitivity to a specific antigen. Thus, the invention embraces the treatment of pathological conditions where an immune response is needed or an immune deficiency must be corrected via administering an amount of the transfer factor to a non-sensitized individual in an amount sufficient to provoke expression of cell mediated immunity against an antigen.

EXAMPLE 27

Treatment of Chronic or Recurrent Herpes Simplex Infections with Herpes-specific Transfer Factor Subject for this treatment have culture-proved cutaneous, labial and/or genital infections with HSV-1 or HSV-2. The dosage for recipients of transfer factor extracted from immune lymphocytes is 5×10[8] lymphocyte equivalents. This is approximately 50 ng of substantially pure transfer factor prepared according to the protocol outlined in Examples 1 through 20 herein. Recipients of synthesized transfer factor receive approximately 50 ng of material at each treatment. All preparations have potency testing by the quantitative footpad swelling assay described above. The injections are given monthly. Monitoring of responses is done with a lesion and symptom score card and by monitoring cell-mediated immune responses to Herpes simplex antigens.

EXAMPLE 28

Treatment of Chronic Mucocutaneous Candidiasis with Specific Transfer Factor

The general protocol is modeled after that used by Kirkpatrick and Greenberg.[52] The subjects are first treated with an antifungal agent such as amphotericin B, fluconazole, or Ketoconazole to reduce the burden of infecting organisms.

[52]Kirkpatrick et al. in Khan et al., ed., *Immune Regulators In Transfer Factor*, pg. 547–559 (Academic Press, 1979)

Specific transfer factor therapy with material extracted from immune lymphocytes requires a dosage of 6×10[8] lymphocyte equivalents. This dosage translates into approximately 60 ng of purified transfer factor and this is the dosage that is used for synthetic transfer factor. Patients receive this dosage monthly for months 1, 2, 3 and 4; then every other month for months 6, 8, 10, and 12. Subsequently, treatments with the same dosage are given at 4 month intervals to maintain remission.

EXAMPLE 29

Treatment of Mycobacterial and Fungal Infections with Transfer Factors

The rationale for use of an immunologically oriented therapy in these patients is based on the observations that cell-mediated immunity and microbiocidal activity may be deficient. The mechanisms producing the immune deficiency are only partially understood and it is probable that there are somewhat different mechanisms in patients with different infections.

Treatment with specific transfer factor employs 5×10[8] lymphocyte equivalents (50 ng of substantially pure transfer factor) per dosage. Treatment with synthetic transfer factors employs 1.2 pgm of material that is specific for the infection that affects the patient. The actual dosage of each lot is determined by a potency assay using the quantitative foot pad assay. Treatments are administered at monthly intervals and continued until the infection is cured.

It should be understood that the foregoing relates only to a preferred embodiment of the present invention and that numerous modifications or alterations may be made without departing from the spirit and scope of the invention as set forth in the appended claims.

We claim:

1. A method of producing substantially pure transfer factor comprising the steps of:
   a. contacting a transfer factor-containing sample with an immobilized antigen to which the transfer factor binds specifically under conditions favoring binding of antigen-specific transfer factor to the antigen to form a transfer factor:antigen complex;
   b. separating the antigen-specific transfer factor from the complex;
   c. applying the separated antigen-specific transfer factor onto a reversed phase, high performance liquid chromatography column; and
   d. eluting a substantially pure transfer factor containing fraction;
   e. selecting the transfer factor containing fraction by monitoring increased absorption at about 214 nm, the substantially pure transfer factor having a specific activity of at least 5,000 units per absorbance unit at 214 nm.

2. The method of claim 1, wherein transfer factor-containing sample is first filtered through a filtering means having a molecular weight cut off point of more than about 6,000 Daltons.

3. The method of claim 1, wherein the specific activity is at least 10,000 units per absorbance unit at 214 nm.

4. The method of claim 1, wherein the specific activity is at least 20,000 units per absorbance unit at 214 nm.

5. The method of claim 1, wherein the specific activity is at least 60,000 units per absorbance unit at 214 nm.

6. The method of claim 1, wherein the substantially pure transfer factor containing sample is a cell lysate.

7. A method of producing substantially pure transfer factor comprising the steps of:
   a. contacting a transfer factor-containing sample with an immobilized antigen to which the transfer factor binds specifically under conditions favoring binding of antigen-specific transfer factor to the antigen to form a transfer factor:antigen complex;
   b. separating the antigen-specific transfer factor from the complex;
   c. applying the separated antigen-specific transfer factor onto a gel filtration, high performance liquid chromatography column; and
   d. eluting a substantially pure transfer factor containing fraction;
   e. selecting the transfer factor containing fraction by monitoring increased absorption at about 214 nm, the substantially pure transfer factor having a specific activity of at least 5,000 units per absorbance unit at 214 nm.

8. The method of claim 7, wherein the transfer factor-containing sample is first filtered through a filtering means having a molecular weight cut off point of more than about 6,000 Daltons.

9. The method of claim 7, wherein the specific activity is at least 10,000 units per absorbance unit at 214 nm.

10. The method of claim 7, wherein the specific activity is at least 20,000 units per absorbance unit at 214 nm.

11. The method of claim 7, wherein the specific activity is at least 60,000 units per absorbance unit at 214 nm.

12. The method of claim 7, wherein the substantially pure transfer factor containing sample is a cell lysate.

13. A method of producing substantially pure transfer factor comprising the steps of:
   a. contacting a transfer factor-containing sample with an immobilized antigen to which the transfer factor binds specifically under conditions favoring binding of antigen-specific transfer factor to the antigen to form a transfer factor:antigen complex;
   b. separating the antigen-specific transfer factor from the complex;
   c. applying the separated antigen-specific transfer factor onto a first reversed phase, high performance liquid chromatography column;
   d. eluting the antigen-specific transfer factor from the first reversed phase, high performance liquid chromatography column;
   e. applying the antigen-specific transfer factor onto a second, gel filtration, high performance liquid chromatography column; and
   f. eluting a substantially pure transfer factor containing fraction from the second high performance liquid chromatography column;
   g. selecting the transfer factor containing fraction by monitoring increased absorption at about 214 nm, the transfer factor having a specific activity of at least 5,000 units per absorbance unit at 214 nm.

14. The method of claim 13, wherein the transfer factor-containing sample is first filtered through a filtering means having a molecular weight cut off point of more than about 6,000 Daltons.

15. The method of claim 13, wherein the specific activity is at least 10,000 units per absorbance unit at 214 nm.

16. The method of claim 13, wherein the specific activity is at least 20,000 units per absorbance unit at 214 nm.

17. The method of claim 13, wherein the specific activity is at least 60,000 units per absorbance unit at 214 nm.

18. The method of claim 13, wherein the transfer factor containing sample is a cell lysate.

19. A method of producing substantially pure transfer factor comprising the steps of:
   a. contacting a transfer factor-containing sample with an immobilized antigen to which the transfer factor binds specifically under conditions favoring binding of antigen-specific transfer factor to the antigen to form a transfer factor:antigen complex;
   b. separating the antigen-specific transfer factor from the complex;
   c. applying the antigen-specific transfer factor onto a first, gel filtration, high performance liquid chromatography column;
   d. eluting the substantially pure transfer factor from the first, gel filtration, high performance liquid chromatography column;
   e. applying the separated antigen-specific transfer factor onto a second reversed phase high performance liquid chromatography column; and
   f. eluting a substantially pure transfer factor containing fraction from the second reversed phase, high performance liquid chromatography column;
   g. selecting the transfer factor containing fraction by monitoring increased absorption at about 214 nm, the substantially pure transfer factor having a specific activity of at least 5,000 units per absorbance unit at 214 nm.

20. The method of claim 19, wherein the transfer factor-containing sample is first filtered through a filtering means having a molecular weight cut off point of more than about 6,000 Daltons.

21. The method of claim 19, wherein the specific activity is at least 10,000 units per absorbance unit at 214 nm.

22. The method of claim 19, wherein the specific activity is at least 20,000 units per absorbance unit at 214 nm.

23. The method of claim 19, wherein the specific activity is at least 60,000 units per absorbance unit at 214 nm.

24. The method of claim 19, wherein the transfer factor containing sample is a cell lysate.

* * * * *